(12) United States Patent
Roy et al.

(10) Patent No.: US 10,561,785 B2
(45) Date of Patent: Feb. 18, 2020

(54) METHOD AND/OR SYSTEM FOR CLOSED-LOOP CONTROL OF GLUCOSE TO A TREATMENT RANGE

(75) Inventors: Anirban Roy, Encino, CA (US); Cesar C. Palerm, Pasadena, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 279 days.

(21) Appl. No.: 12/820,944

(22) Filed: Jun. 22, 2010

(65) Prior Publication Data

US 2011/0313390 A1   Dec. 22, 2011

(51) Int. Cl.
*A61M 5/158* (2006.01)

(52) U.S. Cl.
CPC .................. *A61M 5/158* (2013.01)

(58) Field of Classification Search
CPC .......... A61M 5/1723; A61M 2230/201; A61M 5/14244; A61M 2005/14208; A61M 2005/1726; G06F 19/3468; A61B 5/14532; A61B 5/1427; A61B 5/14503
USPC .............. 604/504; 340/573.1; 703/2; 706/52
See application file for complete search history.

(56) References Cited

U.S. PATENT DOCUMENTS

| | | | |
|---|---|---|---|
| 4,206,755 A * | 6/1980 | Klein | A61M 5/1723 600/368 |
| 5,391,250 A | 2/1995 | Cheney, II et al. | |
| 6,254,586 B1 | 7/2001 | Mann et al. | |
| 6,360,888 B1 | 3/2002 | McIvor et al. | |
| 6,424,847 B1 | 7/2002 | Mastrototaro et al. | |
| 6,554,798 B1 | 4/2003 | Mann et al. | |
| 6,558,320 B1 | 5/2003 | Causey, III et al. | |
| 6,558,351 B1 * | 5/2003 | Steil | A61B 5/14532 604/131 |
| 6,641,533 B2 | 11/2003 | Causey, III et al. | |
| 6,895,263 B2 | 5/2005 | Shin et al. | |
| 7,204,823 B2 | 4/2007 | Estes et al. | |
| 7,267,655 B1 | 9/2007 | Lyapko | |
| 7,399,277 B2 | 7/2008 | Saidara et al. | |
| 7,785,313 B2 | 8/2010 | Mastrototaro | |
| 7,833,157 B2 | 11/2010 | Gottlieb | |
| 7,972,296 B2 | 7/2011 | Braid et al. | |

(Continued)

FOREIGN PATENT DOCUMENTS

| | | |
|---|---|---|
| CA | 2800828 | 12/2011 |
| CN | 102946923 A | 2/2013 |

(Continued)

OTHER PUBLICATIONS

PCT/US2011/039762/ PCT application as filed on Jun. 9, 2011, 55 pages.

(Continued)

*Primary Examiner* — Nathan R Price
*Assistant Examiner* — Weng Lee
(74) *Attorney, Agent, or Firm* — Berkeley Law & Technology Group, LLP

(57) ABSTRACT

Subject matter disclosed herein relates to monitoring and/or controlling blood glucose levels in patients. In particular, one or more substances may be delivered to a patient at a particular infusion rate while the patient's estimated glucose level is within a predetermined range. A different insulin infusion rate may then be applied if the patient's estimated blood glucose level deviates outside of the predetermined range.

17 Claims, 11 Drawing Sheets

(56) References Cited

U.S. PATENT DOCUMENTS

| | | | |
|---|---|---|---|
| 8,152,789 B2* | 4/2012 | Starkweather | A61M 5/172 604/504 |
| 8,579,879 B2 | 11/2013 | Palerm | |
| 2003/0028089 A1* | 2/2003 | Galley | A61B 5/14532 600/365 |
| 2003/0208114 A1 | 11/2003 | Ackerman | |
| 2003/0212379 A1 | 11/2003 | Bylund et al. | |
| 2006/0173406 A1 | 8/2006 | Hayes et al. | |
| 2006/0264895 A1 | 11/2006 | Flanders | |
| 2008/0183060 A1 | 7/2008 | Steil | |
| 2008/0221509 A1 | 9/2008 | Gottlieb et al. | |
| 2008/0269723 A1 | 10/2008 | Mastrototaro | |
| 2008/0275384 A1* | 11/2008 | Mastrototaro | A61B 5/14532 604/66 |
| 2009/0105636 A1* | 4/2009 | Hayter | A61M 5/1723 604/66 |
| 2010/0168660 A1 | 7/2010 | Galley et al. | |
| 2010/0295686 A1* | 11/2010 | Sloan et al. | 340/573.1 |
| 2010/0298686 A1 | 11/2010 | Reggiardo et al. | |

FOREIGN PATENT DOCUMENTS

| | | |
|---|---|---|
| WO | 2000/010628 | 3/2000 |
| WO | 2004/060455 | 7/2004 |
| WO | 2007/149533 | 12/2007 |
| WO | 2008/157780 | 12/2008 |

OTHER PUBLICATIONS

PCT/US2011/000284/ International Search Report and written opinion dated Sep. 21, 2011, 25 pages.
Hovorka et al. "Nonlinear Model Predictive Control of Glucose Concentration in Subjects with Type 1 Diabetes", Institute of Physics Publishing, 2004, pp. 905-920.
Mudaliar et al. "Insulin Aspart (B28-Asp-Insulin): A Fast-Acting Analog of Human Insulin", Diabetes Care, vol. 22, No. 9, Sep. 1999, pp. 1501-1506.
Magni et al. "Run-to-Run Tuning of Model Predictive Control for Type 1 Diabetes Subjects: In Silico Trial", Journal of Diabetes Science and Technology, vol. 3, Issue 5, Sep. 2009, pp. 1091-1098.
Kovatchev et al. "Control to Range for Diabetes: Functionality and Modular Architecture", Journal of Diabetes Science and Technology, vol. 3, Issue 5, Sep. 2009, pp. 1058-1065.
Co-pending U.S. Appl. No. 12/565,574, filed Sep. 23, 2009, entitled "Semi-Closed Loop Insulin Delivery", 42 pages.
Co-pending U.S. Appl. No. 12/486,708, filed Jun. 17, 2009, entitled "Closed-Loop Glucose and/or Insulin Control System", 163 pages.
Co-pending U.S. Appl. No. 12/709,437, filed Feb. 19, 2010, entitled "Closed-Loop Glucose Control Startup", 104 pages.
PCT/US2011/039762/ International Preliminary Report on Patentability, dated Dec. 28, 2012, 10 pages.
Khan, S.E., "Quantification of the relationship between insulin sensititivy and beta-cell function in human subjects. Evidence for a hyperbolic function", Diabetes, Nov. 1993; 42(11) pp. 1663-1672.
Kollind, M., "Insulin clearance during hypoglycemia in patients with insulin-dependent diabetes mellitus", Horm Metab Res, Jul. 1991; 23(7) pp. 333-335.
Lee, H., et al, "A Closed-Loop Artificial Pancreas Using Model Predictive Control and a Sliding Meal Size Estimator" Journal of Diabetes Science and Technology, vol. 3 No. 5, Sep. 2009, pp. 1082-1090.
Marchetti, G. et al., "An Improved PID Switching Control Strategy for Type 1 Diabetes", IEEE Transactions on Biomedical Engineering, vol. 35. No. 3, Mar. 1, 2008, pp. 857-863.
Van Den Berghe, Greet, et al; "Intensive Insulin Therapy in Critically Ill Patients", The New England Journal of Medicine, vol. 345, No. 19, Nov. 8, 2001, pp. 1359-1367.

Weinzimer, Stuart, et al., "Fully Automated Closed-Loop Insulin Delivery Versus Semiautomated Hyprid Control in Pediatric Patients with Type 1 Diabetes Using an Artificial Pancreas" Diabetes Care, American Diabetes Association, vol. 31, No. 5, May 5, 2008, pp. 934-939.
U.S. Appl. No. 12/565,574, filed Sep. 23, 2009, 46 pages.
U.S. Appl. No. 12/565,574, filed Oct. 14, 2009, 3 pages.
U.S. Appl. No. 12/565,574 / Requirement for Restriction/Election, dated Oct. 5, 2010, 8 pages.
U.S. Appl. No. 12/565,574 / Response to Election/Restriction Filed and Amendments, dated Nov. 4, 2010, 12 pages.
U.S. Appl. No. 12/565,574 / Non-Final Rejection, dated Jan. 21, 2011, 10 pages.
U.S. Appl. No. 12/565,574 / Notice of Publication, dated Mar. 24, 2011, 1 page.
U.S. Appl. No. 12,565,574 / Amendment/Req Reconsideration—After Non-Final Rejection, dated Apr. 19, 2011, 17 pages.
U.S. Appl. No. 12/565,574 / Final Rejection, dated Aug. 5, 2011, 13 pages.
U.S. Appl. No. 12/565,574 / RCE and Amendments, dated Nov. 7, 2011, 22 pages.
U.S. Appl. No. 12/565,574 / Non-Final Rejection, dated Dec. 18, 2012, 10 pages.
U.S. Appl. No. 12/565,574 / Amendment/Req Reconsideration—After Non-Final Rejection, dated Mar. 18, 2013, 17 pages.
U.S. Appl. No. 12/565,574 / Final Rejection, dated Nov. 7, 2013, 12 pages.
U.S. Appl. No. 12/565,574 / Abandonment, dated Jun. 13, 2014, 2 pages.
PCT/US2010/002506/ PCT application as filed on Sep. 15, 2010, 38 pages.
PCT/US2010/002506/ Initial Publication without International Search Report, dated Mar. 31, 2011, 38 pages.
PCT/US2010/002506/ International Search Report, dated May 19, 2011, 6 pages.
PCT/US2010/002506/ Written Opinion of the International Search Authority, dated Mar. 23, 2012, 10 pages.
PCT/US2010/002506/ International Preliminary report on patentability, dated Mar. 27, 2012, 11 pages.
U.S. Appl. No. 12/486,708, filed Jun. 17, 2009, 167 pages.
U.S. Appl. No. 12/486,708/Applicant Response to Pre-Exam Formalities Notice, dated Sep. 9, 2009, 262 pages.
U.S. Appl. No. 12/486,708, filed Jul. 9, 2009, 3 pages.
U.S. Appl. No. 12/486,708, filed Sep. 22, 2009, 3 pages.
U.S. Appl. No. 12/486,708/Notice of Publication, dated Dec. 23, 2010, 1 page.
U.S. Appl. No. 12/486,708/Requirement for Restriction/Election, dated Dec. 21, 2011, 15 pages.
U.S. Appl. No. 12/486,708/Response to Election/Restriction, dated Jan. 19, 2012, 16 pages.
U.S. Appl. No. 12/486,708/Non-Final Rejection, dated Feb. 9, 2012, 14 pages.
U.S. Appl. No. 12/486,708/Amendment/Req. Reconsideration—After Non-Final Rejection, dated Jun. 9, 2012, 21 pages.
U.S. Appl. No. 12/486,708/Final Rejection, dated Jul. 16, 2012, 15 pages.
U.S. Appl. No. 12/486,708/RCE and Amendments, dated Oct. 10, 2012, 24 pages.
U.S. Appl. No. 12/486,708/Non-Final Rejection, dated Sep. 17, 2013, 16 pages.
U.S. Appl. No. 12/486,708/Amendment/Req. Reconsideration—After Non-Final Rejection, dated Dec. 12, 2013, 18 pages.
U.S. Appl. No. 12/486,708/Final Rejection, dated Jan. 24, 2014, 17 pages.
U.S. Appl. No. 12/486,708/Response After Final Action and Amendments, dated Mar. 20, 2014, 20 pages.
U.S. Appl. No. 12/486,708/Advisory Action, dated Apr. 2, 2014, 4 pages.
U.S. Appl. No. 12/486,708/Notice of Appeal, dated Apr. 24, 2014, 1 page.
U.S. Appl. No. 12/486,708/Appeal Brief Filed, dated Jun. 23, 2014, 45 pages.

(56) References Cited

OTHER PUBLICATIONS

U.S. Appl. No. 12/486,708/Examiner's Answer to Appeal Brief, dated Jul. 29, 2014, 16 pages.
U.S. Appl. No. 12/486,708/Reply Brief Filed Sep. 19, 2014, 15 pages.
PCT/US2010/001751 / PCT application as filed on Jun. 17, 2010, 153 pages.
PCT/US2010/001751 / Initial Publication without International Search Report dated Dec. 23, 2010, 153 pages.
PCT/US2010/001751 / International Search Report dated Jan. 14, 2011, 7 pages.
PCT/US2010/001751 / Written Opinion of the International Search Authority, dated Dec. 20, 2011, 13 pages.
PCT/US2010/001751 / International Preliminary Report on Patentability, dated Dec. 20, 2011, 14 pages.
EP10729731 / Communication pursuant to Rules 161(1) and 162 EPC, dated Jan. 24, 2012, 2 pages.
PCT/US2011/000284/ PCT application as filed on Feb. 16, 2011, 76 pages.
PCT/US2011/000284/ Initial Publication with International Search Report dated Aug. 25, 2011, 77 pages.
PCT/US2011/000284/ International Search Report dated Jul. 12, 2011, 2 pages.
U.S. Appl. No. 12/709,437, filed Feb. 19, 2010, 108 pages.
U.S. Appl. No. 12/709,437, filed Mar. 18, 2010, 3 pages.
U.S. Appl. No. 12/709,437 / Notice of Publication, dated Aug. 25, 2011, 3 pages.
U.S. Appl. No. 12/709,437 / Requirement for Restriction/Election, dated May 25, 2012, 7 pages.
U.S. Appl. No. 12/709,437 / Response to Election/Restriction and Amendments, dated Jun. 21, 2012, 18 pages.
U.S. Appl. No. 12/709,437 / Non-Final Rejection, dated Oct. 4, 2012, 14 pages.
U.S. Appl. No. 12/709,437 / Amendment/Req Reconsideration—After Non-Final Rejection, dated Jan. 3, 2013.
U.S. Appl. No. 12/709,437 / Notice of Allowance and Fees, dated Jul. 9, 2013, 9 pages.
U.S. Appl. No. 12/709,437 / Issue Fee Payment, dated Oct. 7, 2013, 2 pages.
U.S. Appl. No. 12/709,437 / Issue Notification, dated Oct. 23, 2013, 1 page.
EP/2585133/ Amendments to Claims After Search Report, dated Nov. 22, 2012, 11 pages.
EP/2585133/ Amendments to Claims After Search Report, dated Nov. 28, 2012, 11 pages.
CN/102946923/ First Office Action, dated Apr. 18, 2014, 14 pages.
CN/102946923/ Fourth Office Action, dated Feb. 15, 2016, 9 pages.
JP/2013-529500/ Notice of Grounds for Rejection, dated Mar. 25, 2014, 3 pages.
U.S. Appl. No. 12/486,708/Patent Board Decision, dated Nov. 17, 2016, 8 pages.
Examiner's Report dated Mar. 3, 2017, CA appl'n 2,800,828, 3 pages.
CN App No. 201180029766.7, (PCT/US2011/039762) / Rejection Decision and English Translation, dated Jul. 18, 2016, 10 pages.
EP App No. 11726610.6 / Communication pursuant to Article 94(3) EPC, dated Oct. 7, 2016, 5 pages.
EP App No. 11726610.6 / Reply and Amendment, dated Feb. 7, 2017, 5 pages.
Canadian appl'n 2800828, (PCT/US2011/039762) / Amendment/ Remarks in Response to Examiner's Report, filed Aug. 1, 2017, 9 pages.
Examiner's Report, dated Oct. 2, 2017, CA Appl'n. 2,800,828 3 pages.
Communication under Rule 71(3) EPC, dated Oct. 17, 2017; EP Appl'n. 11 726 610.6-1666; 52 pages.
CA Appl'n 2,800,828; Office Action dated Apr. 30, 2018, 4 pages.
Transmission dated Jun. 11, 2018 of patent certificate for EP Patent No. 2585133, 3 pages.
PCT/US2011/039762: Amendment filed Mar. 5, 2018, 10 pages.
App. 11 726 610.6-1666: Reply to Communication under Rule 71(3) EPC, dated Jan. 11, 2018, 5 pages.
App. 11 726 610.6-1666: Communication under Rule 71(3) EPC, dated Mar. 6, 2018, 52 pages.
App. CN102946923: CN Patent # ZL 201180019766.7, granted, dated Dec. 12, 2017 (partially translated), 34 pages.
CA Appl'n No. 2800828 / OA Response, dated Oct. 16, 2018, 13 pages.
CA Appl'n. No. 2800828 / Notice of Allowance, dated Jan. 18, 2019, 1 page.
CA Appl'n. No. 2800828 / Amendment/Remarks in Response to Examiner's Report, dated Oct. 16, 2018, 13 pages.

\* cited by examiner

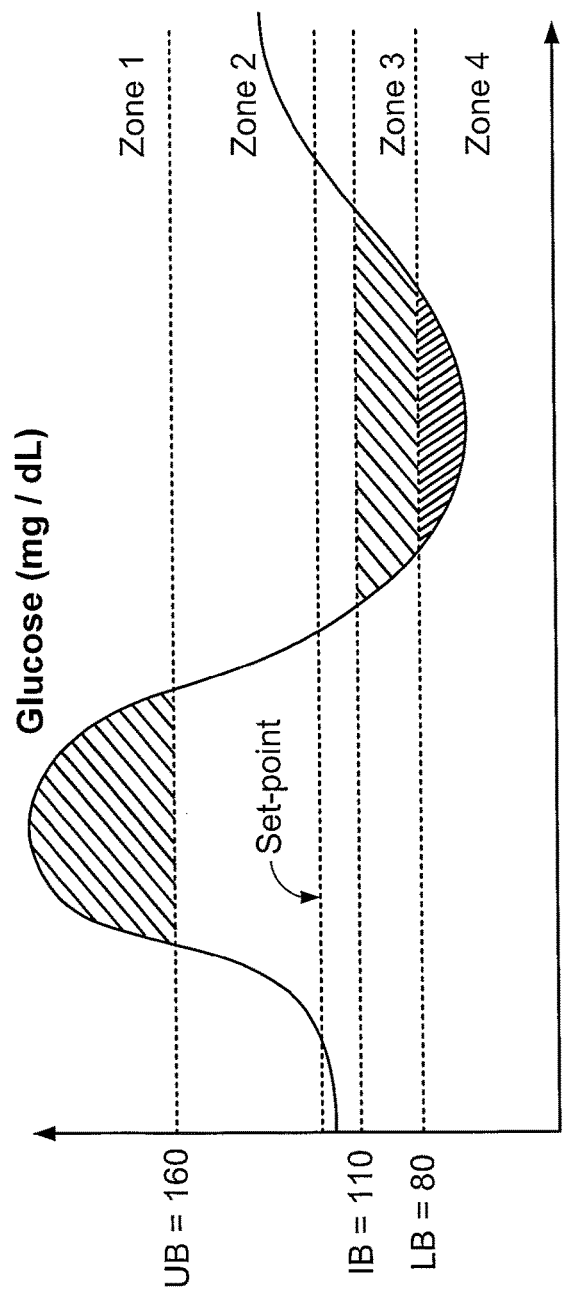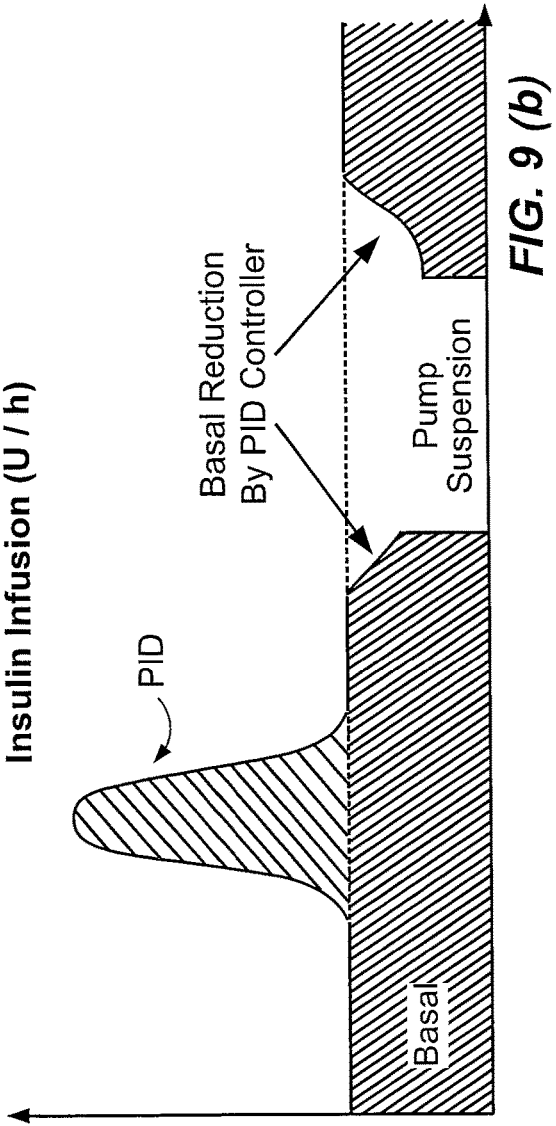
FIG. 9 (a)
FIG. 9 (b)

METHOD AND/OR SYSTEM FOR CLOSED-LOOP CONTROL OF GLUCOSE TO A TREATMENT RANGE

BACKGROUND

1. Field

Subject matter disclosed herein relates to monitoring and/or controlling blood glucose levels in patients.

2. Information

The pancreas of a normal healthy person produces and releases insulin into the blood stream in response to elevated blood plasma glucose levels. Beta cells (β-cells), which reside in the pancreas, produce and secrete insulin into the blood stream as it is needed. If β-cells become incapacitated or die, a condition known as Type 1 diabetes mellitus (or in some cases, if β-cells produce insufficient quantities of insulin, a condition known as Type 2 diabetes), then insulin may be provided to a body from another source to maintain life or health.

Traditionally, because insulin cannot be taken orally, insulin has been injected with a syringe. More recently, the use of infusion pump therapy has been increasing in a number of medical situations, including for delivering insulin to diabetic individuals. For example, external infusion pumps may be worn on a belt, in a pocket, or the like, and they can deliver insulin into a body via an infusion tube with a percutaneous needle or a cannula placed in subcutaneous tissue.

As of 1995, less than 5% of Type 1 diabetic individuals in the United States were using infusion pump therapy. Presently, over 7% of the more than 900,000 Type 1 diabetic individuals in the U.S. are using infusion pump therapy. The percentage of Type 1 diabetic individuals that use an infusion pump is growing at a rate of over 2% each year. Moreover, the number of Type 2 diabetic individuals is growing at 3% or more per year, and growing numbers of insulin-using Type 2 diabetic individuals are also adopting infusion pumps. Additionally, physicians have recognized that continuous infusion can provide greater control of a diabetic individual's condition, so they too are increasingly prescribing it for patients.

A closed-loop infusion pump system may include an infusion pump that is automatically and/or semi-automatically controlled to infuse insulin into a patient. The infusion of insulin may be controlled to occur at times and in amounts that are based, for example, upon blood glucose measurements obtained from an embedded glucose sensor in real-time. Closed-loop infusion pump systems may also employ the delivery of glucose and/or glucagon, in addition to the delivery of insulin, for controlling blood-glucose levels of a patient (e.g., in a hypoglycemic context).

SUMMARY

Briefly, example embodiments may relate to methods, systems, apparatuses, and/or articles, etc. for establishing a range about a blood glucose set-point for a patient; delivering insulin to the patient at a basal insulin delivery rate while the patient's estimated glucose level is within the range; and selectively applying a different insulin delivery rate to the patient while the estimated glucose level is outside of the range. Here, the different insulin delivery rate being calculated based, at least in part, on the set-point.

In another particular implementation, the different insulin infusion rate is based, at least in part, on a PID algorithm.

In yet another implementation the different insulin infusion rate may be selectively applied in response to a prediction that a patient's glucose level is to be outside of range.

In yet another implementation, the different insulin infusion rate is less than the basal rate if said estimated glucose level is below said range. For example, the different insulin infusion rate may be set to a zero insulin infusion rate.

In yet another implementation an insulin delivery rate may be selectively applied based, at least in part, on a PID algorithm if the estimated blood glucose level is within said range and decreasing at a rate exceeding a threshold.

In yet another implementation, the basal insulin delivery rate may be selectively applied while the estimated glucose level is above said range if insulin delivered to said patient over a sliding window exceeds a threshold amount.

In yet another embodiment, the blood glucose set-point is determined based, at least in part, on a reference trajectory.

In yet another embodiment, a system may receive commands from a patient or caregiver for determining an insulin delivery rate.

In yet another embodiment, commands may be received from said patient to determine insulin delivery. The aforementioned different insulin delivery rate may then be selectively applied in an absence of commands from the patient.

Other alternative example embodiments are described herein and/or illustrated in the accompanying Drawings. Additionally, particular example embodiments may be directed to an article comprising a storage medium including machine-readable instructions stored thereon which, if executed by a special purpose computing device and/or processor, may be directed to enable the special purpose computing device/processor to execute at least a portion of described method(s) according to one or more particular implementations. In other particular example embodiments, a sensor may be adapted to generate one or more signals responsive to a measured blood glucose concentration in a body while a special purpose computing device/processor may be adapted to perform at least a portion of described methods) according to one or more particular implementations based upon one or more signals generated by the sensor.

BRIEF DESCRIPTION OF THE FIGURES

Non-limiting and non-exhaustive features will be described with reference to the following figures, wherein like reference numerals refer to like parts throughout the various figures:

FIG. 3(*b*) is a side cross-sectional view of a glucose sensor system of FIG. 3(*a*) for an embodiment.

FIG. 3(*c*) is a perspective view of an example sensor set of a glucose sensor system of FIG. 3(*a*) for an embodiment.

FIG. 3(*d*) is a side cross-sectional view of a sensor set of FIG. 3(*c*) for an embodiment.

FIG. 9(a) shows an example of changes in estimated blood glucose in a patient according to an embodiment.

FIG. 9(b) shows changes in rates of insulin delivery to a patient responsive to estimated blood glucose in a patient according to an embodiment.

DETAILED DESCRIPTION

Figure 1:
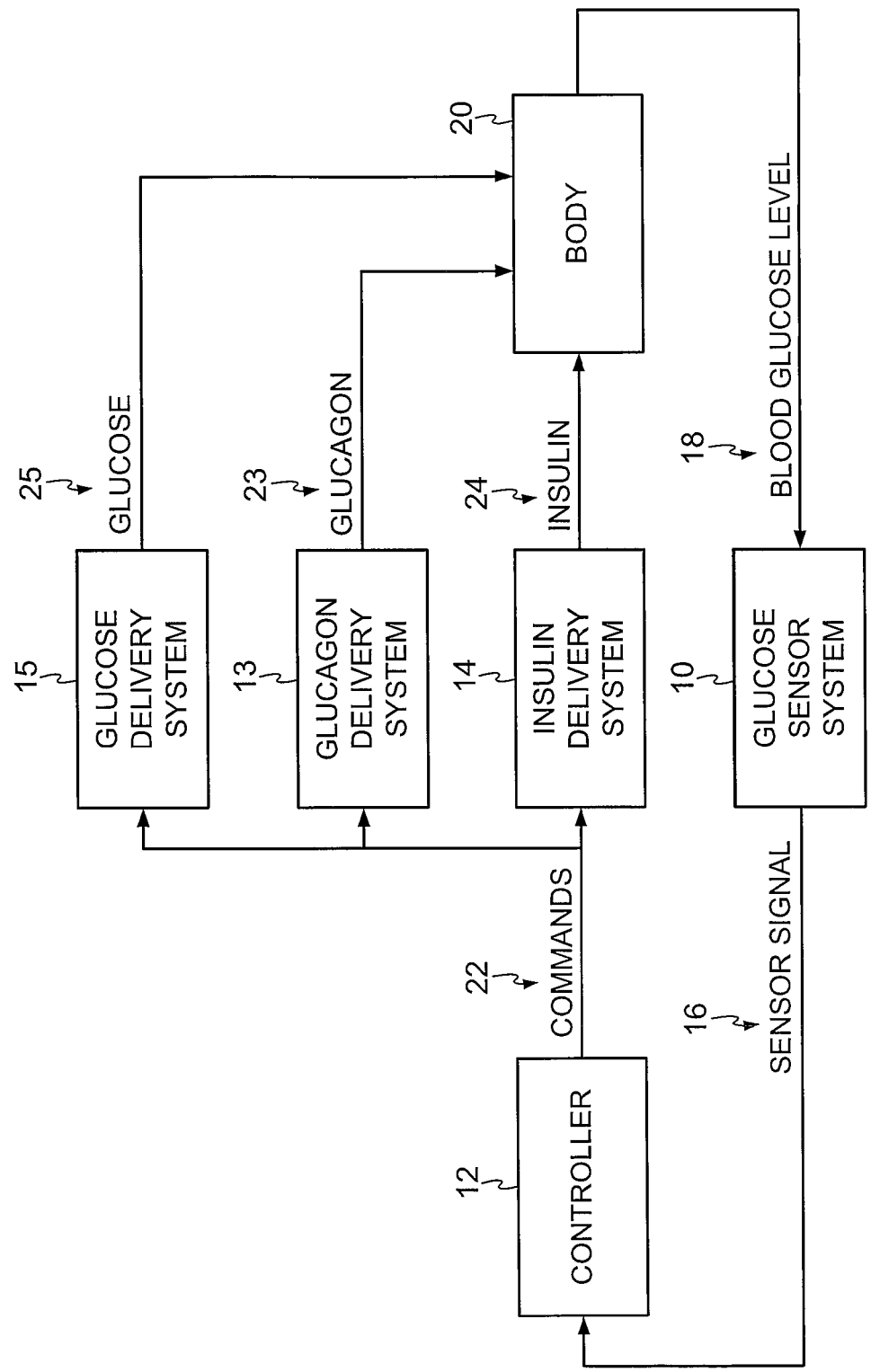
FIG. 1 is a block diagram of an example closed loop glucose control system in accordance with an embodiment.

In an example glucose control system environment, blood-glucose measurements may be employed in a closed loop infusion system for regulating a rate of fluid infusion into a body. In particular example embodiments, a control system may be adapted to regulate a rate of insulin, glucagon, and/or glucose infusion into a body of a patient based, at least in part, on a glucose concentration measurement taken from a body (e.g., from a glucose sensor). In certain example implementations, such a system may be designed to model a pancreatic beta cell (β-cell). Here, such a system may enable a patient to control an infusion device for releasing insulin into the patient's body for effective blood glucose management. In particular embodiments, however, such a system may also be adapted to intervene if such a patient is not responsive to extreme levels of blood glucose, thereby reducing the risk of hypoglycemia and hyperglycemia. Here, such a system may be adapted to control infusion of insulin so as to control/maintain a patient's blood glucose within a target range, thus reducing the risk that a patient's blood glucose level transitions to dangerous extreme levels in the absence of patient action.

According to certain embodiments, examples of closed-loop systems as described herein may be implemented in a hospital environment to monitor and/or control levels of glucose in a patient. Here, as part of a hospital or other medical facility procedure, a caretaker or attendant may be tasked with interacting with a closed-loop system to, for example: enter blood-glucose reference measurements into control equipment to calibrate blood glucose measurements obtained from glucose sensors, make manual adjustments to devices, and/or make changes to therapies, just to name a few examples. Alternatively, according to certain embodiments, examples of closed-loop systems as described herein may be implemented in non-hospital environments to monitor and/or control levels of glucose in a patient. Here, a patient or other non-medical professional may be responsible for interacting with a closed-loop system.

To maintain healthy glucose levels, a person with type 1 diabetes may manage their glycemia by monitoring blood glucose levels, controlling diet, exercise, and self-administering appropriate amounts of insulin at appropriate times. Deviations from such glycemic management, such as skipping an insulin bolus at meal time or underestimating the carbohydrate content of a meal may bring about prolonged hyperglycemia. Likewise, receiving too much insulin (e.g., by over-bolusing) for a given blood glucose level and/or meal may bring about severe hypoglycemia. Other external factors, such as exercise or stress, may also contribute to glycemic deviations.

In a particular embodiment of a closed-loop system, such a system may be adapted to control infusion of insulin so as to control/maintain a patient's blood glucose within a target range, thus reducing the risk that a patient's blood glucose level transition to dangerous extreme levels. Again, such a mechanism may reduce the risk of hypoglycemia and hyperglycemia if a patient, non-medical professional or medical professional is not fully attentive to providing inputs to the system for effective glycemic management.

According to an embodiment, depending on a patient's particular physiology, a target or set-point glucose level may be established. For example, such a target or set-point glucose level may be defined based, at least in part, on guidelines established by the American Diabetes Association (ADA) and/or clinical judgment of a patient's physician. Here, for example, the ADA has recommended a pre-prandial blood glucose concentration of between 80-130 mg/dl, which is in the normal glycemic range. Alternatively, target or set-point glucose level may be fixed at 120 mg/dl. In yet another alternative, a target or set-point blood glucose concentration may vary over time depending on particular patient conditions. It should be understood, however, that these are merely examples of a target or set-point blood glucose concentration, and claimed subject matter is not limited in this respect.

According to an embodiment, a closed-loop system may be employed to maintain a patient's glucose level in a range about a predetermined set-point or target level. Here, insulin may be infused to the patient at a predetermined basal rate while the patient's glucose level is within the predetermined range. If the glucose level escapes that range, a different infusion rate may be applied based, at least in part, on the predetermined set-point or target level. For example, if the patient's glucose level exceeds the range, an infusion rate may be increased. In another example, if the patient's glucose level falls below a particular level, an insulin infusion rate may be reduced from the basal rate. Of course, these are merely examples of how the insulin infusion rate may be changed if a patient's glucose level escapes a particular range, and claimed subject matter is not limited in this respect.

By maintaining a predetermined basal insulin infusion rate while the glucose level is within a target range, extreme glycemic variations may be reduced or avoided altogether. This may provide a patient with improved glycemic control in circumstances in which they would otherwise be exposed to undesirable extremes of glycemia. Here, while such a patient may remain in control of insulin infusion decisions, particular embodiments may respond automatically in the absence of particular patient action (e.g., forgetting to bolus insulin to cover a meal) to prevent blood glucose from reaching extreme levels.

FIG. 1 is a block diagram of an example closed-loop glucose control system in accordance with an embodiment. Particular embodiments may include a glucose sensor system 10, a controller 12, an insulin delivery system 14, a glucagon delivery system 13, and a glucose delivery system 15, as shown in FIG. 1. In certain example embodiments, glucose sensor system 10 may generate a sensor signal 16 representative of blood glucose levels 18 in body 20, and it may provide sensor signal 16 to controller 12. Controller 12 may receive sensor signal 16 and generate commands 22 that are communicated to insulin delivery system 14, glucagon delivery system 13, and/or glucose delivery system 15. Insulin delivery system 14 may receive commands 22 and infuse insulin 24 into body 20 in response to commands 22. Likewise, glucagon delivery system 13 may receive commands 22 and infuse glucagon 23 into body 20 in response to commands 22. Similarly, glucose delivery system 15 may receive commands 22 and infuse glucose 25 into body 20 in response to commands 22.

Glucose sensor system 10 may include a glucose sensor, sensor electrical components to provide power to a sensor and to generate sensor signal 16, a sensor communication system to carry sensor signal 16 to controller 12, and a sensor system housing for electrical components and a sensor communication system. A glucose sensor may measure blood glucose directly from a blood stream, indirectly via interstitial fluid using e.g. a subcutaneous sensor, some combination thereof, and so forth, just to name a few examples. As used herein, "blood glucose", "measured blood glucose", "blood glucose concentration", "measured blood glucose concentration", and the like may refer to a glucose level, a blood glucose level, a blood glucose concentration, and so forth that has been obtained via any type of glucose sensor. It should be understood, however that using a blood glucose sensor is only one particular technique for obtaining such values, and that other techniques, such as measuring blood glucose in other body fluids (e.g., in interstitial fluid using a subcutaneous sensor), may be used without deviating from claimed subject matter.

Controller 12 may include electrical components and software to generate commands 22 for insulin delivery system 14, glucagon delivery system 13, and/or glucose delivery system 15 based on sensor signal 16. Controller 12 may also include a controller communication system to receive sensor signal 16 and provide commands 22 to insulin delivery system 14, glucagon delivery system 13, and/or glucose delivery system 15. In particular example implementations, controller 12 may include a user interface and/or operator interface (not shown) comprising a data input device and/or a data output device. Such a data output device may, for example, generate signals to initiate an alarm and/or include a display or printer for showing status of a controller 12 and/or a patient's vital indicators. Such a data input device may comprise dials, buttons, pointing devices, manual switches, alphanumeric keys, a touch-sensitive display, combinations thereof, and/or the like for receiving user and/or operator inputs. Such a data input device may be used for scheduling and/or initiating insulin bolus injections for meals, for example. It should be understood, however, that these are merely examples of input and output devices that may be a part of an operator and/or user interface and that claimed subject matter is not limited in these respects.

Insulin delivery system 14 may include an infusion device and/or an infusion tube to infuse insulin 24 into body 20. Similarly, glucagon delivery system 13 may include an infusion device and/or an infusion tube to infuse glucagon 23 into body 20. Likewise, glucose delivery system 15 may include an infusion device and/or an infusion tube to infuse glucose 25 into body 20. In alternative embodiments, insulin 24, glucagon 23, and/or glucose 25 may be infused into body 20 using a shared infusion tube. In other alternative embodiments, insulin 24, glucagon 23, and/or glucose 25 may be infused using an intravenous system for providing fluids to a patient (e.g., in a hospital or other medical environment). It should be understood, however, that certain example embodiments may include an insulin delivery system 14 without a glucagon delivery system 13 and/or without a glucose delivery system 15.

In particular embodiments, an infusion device (not explicitly identified in FIG. 1) may include infusion electrical components to activate an infusion motor according to commands 22, an infusion communication system to receive commands 22 from controller 12, and an infusion device housing (not shown) to hold the infusion device.

In particular example embodiments, controller 12 may be housed in an infusion device housing, and an infusion communication system may comprise an electrical trace or a wire that carries commands 22 from controller 12 to an infusion device. In alternative embodiments, controller 12 may be housed in a sensor system housing, and a sensor communication system may comprise an electrical trace or a wire that carries sensor signal 16 from sensor electrical components to controller electrical components. In other alternative embodiments, controller 12 may have its own housing or may be included in a supplemental device. In yet other alternative embodiments, controller 12 may be co-located with an infusion device and a sensor system within a single housing. In further alternative embodiments, a sensor, a controller, and/or infusion communication systems may utilize a cable; a wire; a fiber optic line; RF, IR, or ultrasonic transmitters and receivers; combinations thereof; and/or the like instead of electrical traces, just to name a few examples.

Overview of Example Systems

Figure 2:
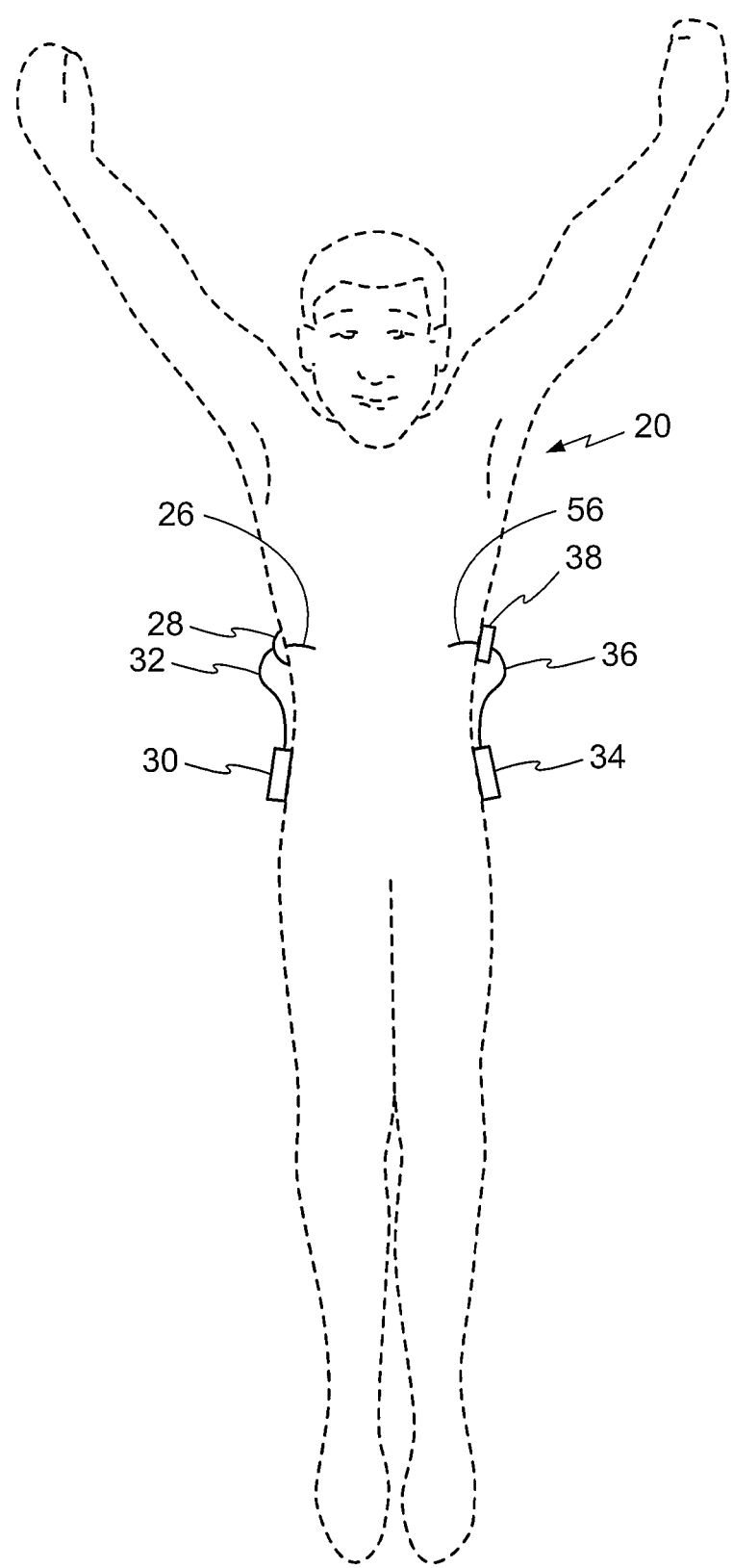
FIG. 2 is a front view of example closed loop hardware located on a body in accordance with an embodiment.
Figure 3:
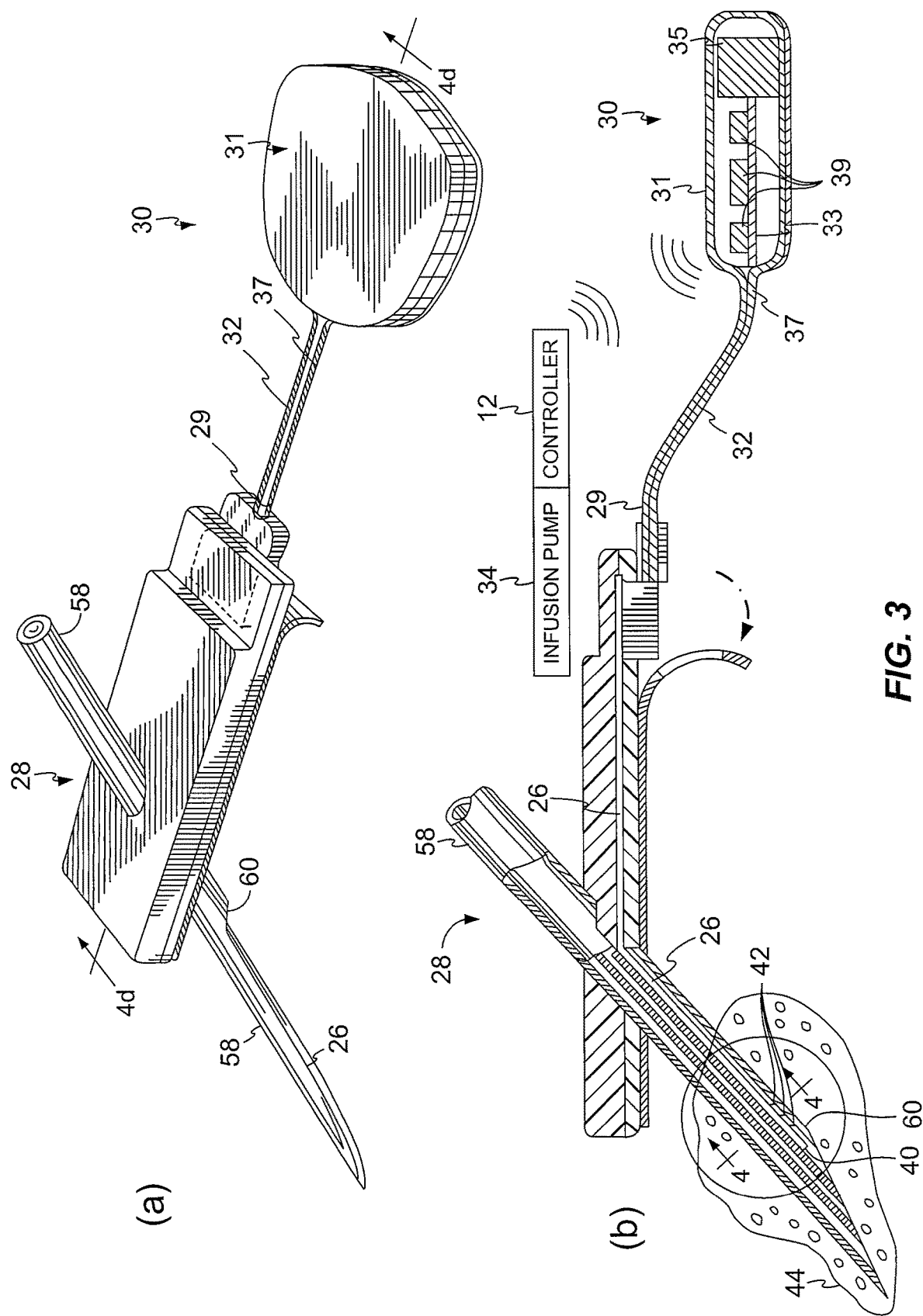
FIG. 3(*a*) is a perspective view of an example glucose sensor system for use in accordance with an embodiment.
Figure 3:
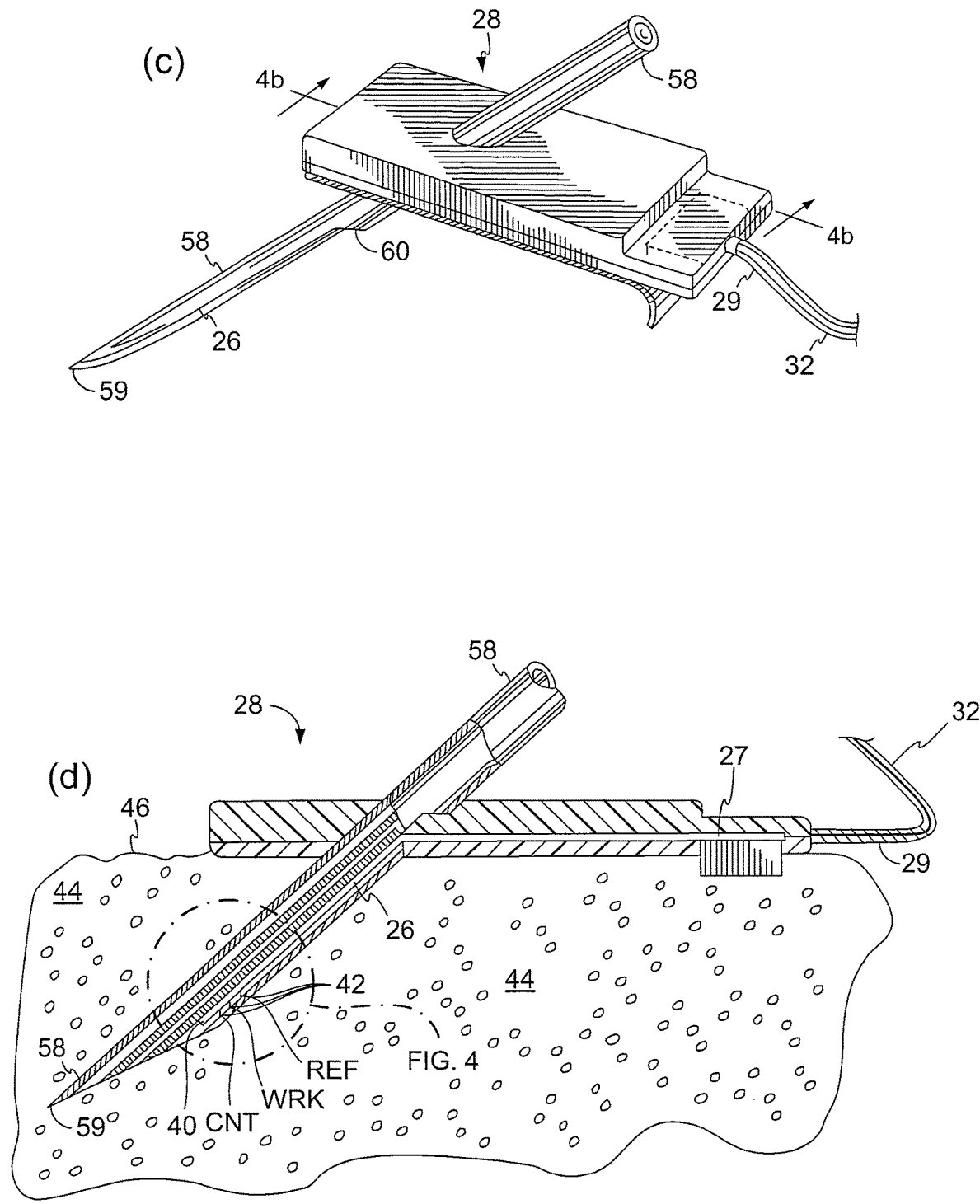
Figure 4:
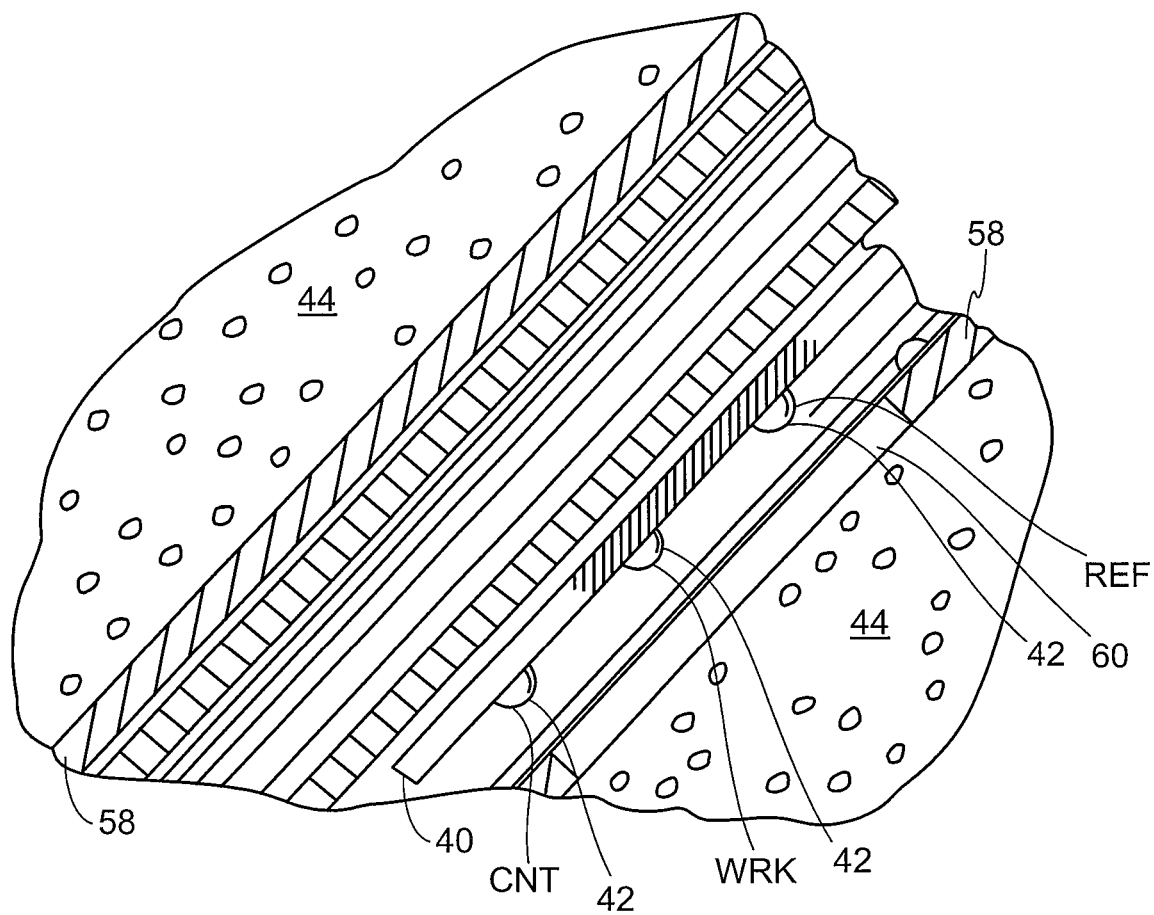
FIG. 4 is a cross sectional view of an example sensing end of a sensor set of FIG. 3(*d*) for an embodiment.
Figure 5:
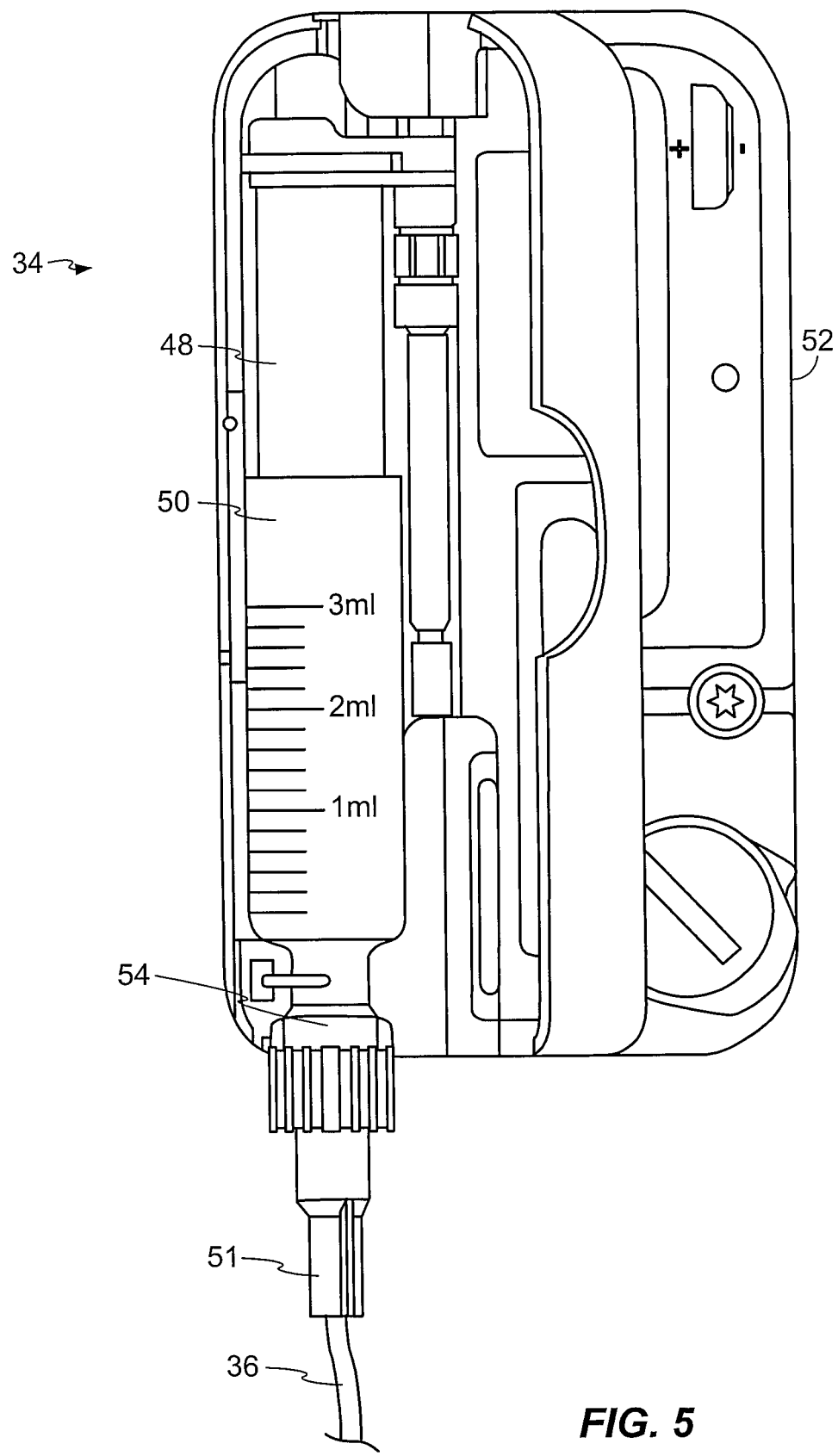
FIG. 5 is a top view of an example infusion device with a reservoir door in an open position, for use according to an embodiment.
Figure 6:
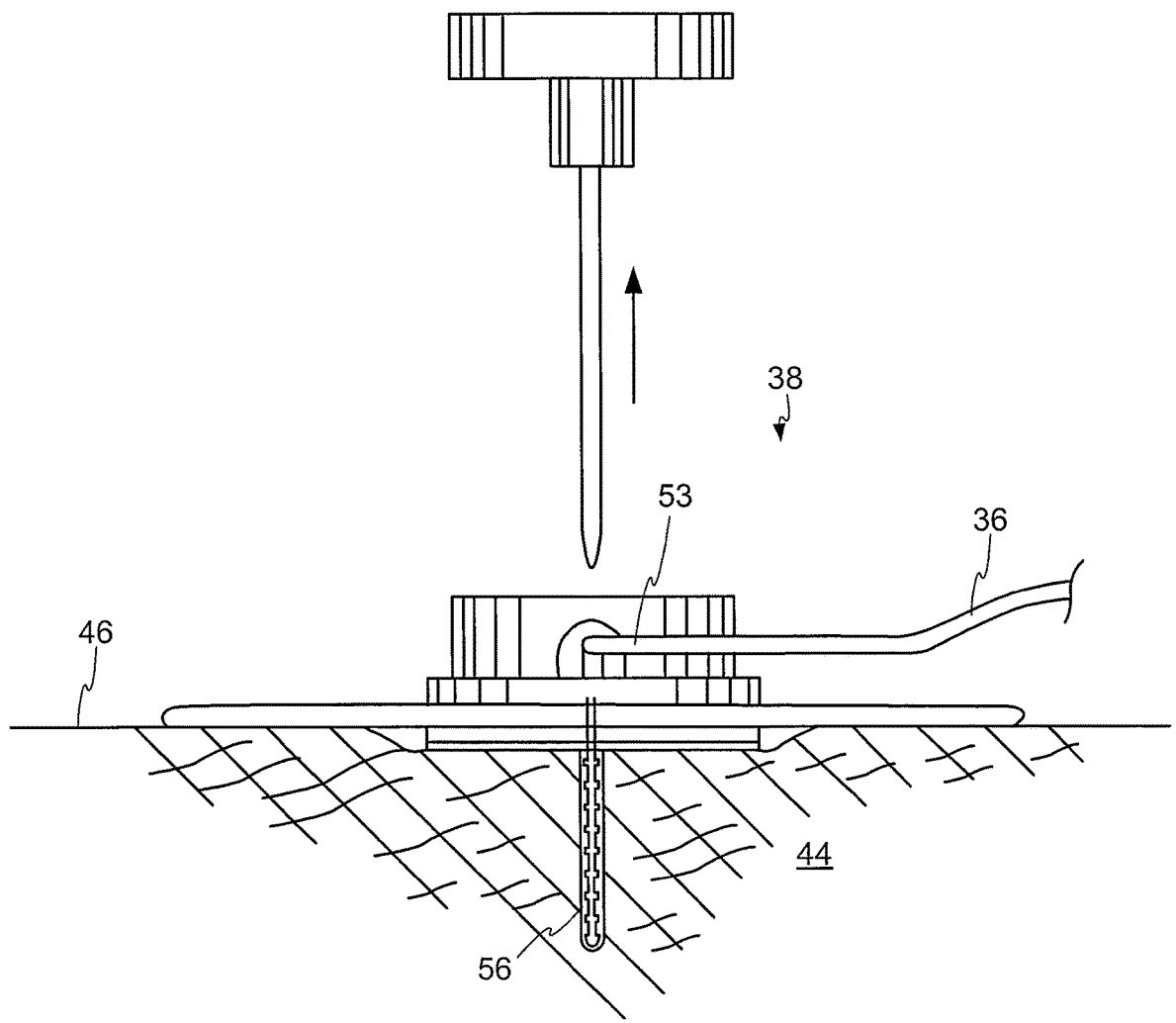
FIG. 6 is a side view of an example infusion set with an insertion needle pulled out, for use according to an embodiment.

FIGS. 2-6 illustrate example glucose control systems in accordance with certain embodiments. Such glucose control systems may be used, for example, in controlling a patient's glucose level about a target range as discussed above. It should be understood, however, that these are merely examples of particular systems that may be use for controlling a patient's glucose level about a target range and that claimed subject matter is not limited in this respect. FIG. 2 is a front view of example closed loop hardware located on a body in accordance with certain embodiments. FIGS. 3(a)-3(d) and 4 show different views and portions of an example glucose sensor system for use in accordance with certain embodiments. FIG. 5 is a top view of an example infusion device with a reservoir door in an open position in accordance with certain embodiments. FIG. 6 is a side view of an example infusion set with an insertion needle pulled out in accordance with certain embodiments.

Particular example embodiments may include a sensor 26, a sensor set 28, a telemetered characteristic monitor 30, a sensor cable 32, an infusion device 34, an infusion tube 36, and an infusion set 38, any or all of which may be worn on a body 20 of a user or patient, as shown in FIG. 2. As shown in FIGS. 3(a) and 3(b), telemetered characteristic monitor 30 may include a monitor housing 31 that supports a printed circuit board 33, battery or batteries 35, antenna (not shown), a sensor cable connector (not shown), and so forth. A sensing end 40 of sensor 26 may have exposed electrodes 42 that may be inserted through skin 46 into a subcutaneous tissue 44 of a user's body 20, as shown in FIGS. 3(d) and 4.

Electrodes 42 may be in contact with interstitial fluid (ISF) that is usually present throughout subcutaneous tissue 44.

Sensor 26 may be held in place by sensor set 28, which may be adhesively secured to a user's skin 46, as shown in FIGS. 3(c) and 3(d). Sensor set 28 may provide for a connector end 27 of sensor 26 to connect to a first end 29 of sensor cable 32. A second end 37 of sensor cable 32 may connect to monitor housing 31. Batteries 35 that may be included in monitor housing 31 provide power for sensor 26 and electrical components 39 on printed circuit board 33. Electrical components 39 may sample sensor signal 16 (e.g., of FIG. 1) and store digital sensor values (Dsig) in a memory. Digital sensor values Dsig may be periodically transmitted from a memory to controller 12, which may be included in an infusion device.

With reference to FIGS. 2 and 5 (and FIG. 1), a controller 12 may process digital sensor values Dsig and generate commands 22 (e.g., of FIG. 1) for infusion device 34. Infusion device 34 may respond to commands 22 and actuate a plunger 48 that forces insulin 24 (e.g., of FIG. 1) out of a reservoir 50 that is located inside an infusion device 34. Glucose may be infused from a reservoir responsive to commands 22 using a similar and/or analogous device (not shown). In alternative implementations, glucose may be administered to a patient orally.

In particular example embodiments, a connector tip 54 of reservoir 50 may extend through infusion device housing 52, and a first end 51 of infusion tube 36 may be attached to connector tip 54. A second end 53 of infusion tube 36 may connect to infusion set 38 (e.g., of FIGS. 2 and 6). With reference to FIG. 6 (and FIG. 1), insulin 24 (e.g., of FIG. 1) may be forced through infusion tube 36 into infusion set 38 and into body 16 (e.g., of FIG. 1). Infusion set 38 may be adhesively attached to a user's skin 46. As part of infusion set 38, a cannula 56 may extend through skin 46 and terminate in subcutaneous tissue 44 to complete fluid communication between a reservoir 50 (e.g., of FIG. 5) and subcutaneous tissue 44 of a user's body 16.

In example alternative embodiments, as pointed out above, a closed-loop system in particular implementations may be a part of a hospital-based glucose management system. Given that insulin therapy during intensive care has been shown to dramatically improve wound healing and reduce blood stream infections, renal failure, and polyneuropathy mortality, irrespective of whether subjects previously had diabetes (See, e.g., Van den Berghe G. et al. NEJM 345: 1359-67, 2001), particular example implementations may be used in a hospital setting to control a blood glucose level of a patient in intensive care. In such alternative embodiments, because an intravenous (IV) hookup may be implanted into a patient's arm while the patient is in an intensive care setting (e.g., ICU), a closed loop glucose control may be established that piggy-backs off an existing IV connection. Thus, in a hospital or other medical-facility based system, IV catheters that are directly connected to a patient's vascular system for purposes of quickly delivering IV fluids, may also be used to facilitate blood sampling and direct infusion of substances (e.g., insulin, glucose, glucagon, etc.) into an intra-vascular space.

Moreover, glucose sensors may be inserted through an IV line to provide, e.g., real-time glucose levels from the blood stream. Therefore, depending on a type of hospital or other medical-facility based system, such alternative embodiments may not necessarily utilize all of the described system components. Examples of components that may be omitted include, but are not limited to, sensor 26, sensor set 28, telemetered characteristic monitor 30, sensor cable 32, infusion tube 36, infusion set 38, and so forth. Instead, standard blood glucose meters and/or vascular glucose sensors, such as those described in co-pending U.S. Patent Application Publication No. 2008/0221509 (U.S. patent application Ser. No. 12/121,647; to Gottlieb, Rebecca et al.; entitled "MULTILUMEN CATHETER"), filed 15 May 2008, may be used to provide blood glucose values to an infusion pump control, and an existing IV connection may be used to administer insulin to an patient. Other alternative embodiments may also include fewer, more, and/or different components than those that are described herein and/or illustrated in the accompanying Drawings.

Example System and/or Environmental Delays

Example system and/or environmental delays are described herein. Ideally, a sensor and associated component(s) would be capable of providing a real time, noise-free measurement of a parameter, such as a blood glucose measurement, that a control system is intended to control. However, in real-world implementations, there are typically physiological, chemical, electrical, algorithmic, and/or other sources of time delays that cause a sensor measurement to lag behind an actual present value. Also, as noted herein, such a delay may arise from, for instance, a particular level of noise filtering that is applied to a sensor signal. Such delays and/or time lags in obtaining sensor glucose measurements may ultimately affect closed-loop operation. Accordingly, and as discussed in greater detail below, feedback control mechanisms using various approaches (e.g., PID, treat-to-target range, model-predictive, etc,) may be used to effectively respond to abrupt changes in a patient's blood glucose concentration.

Figure 7:
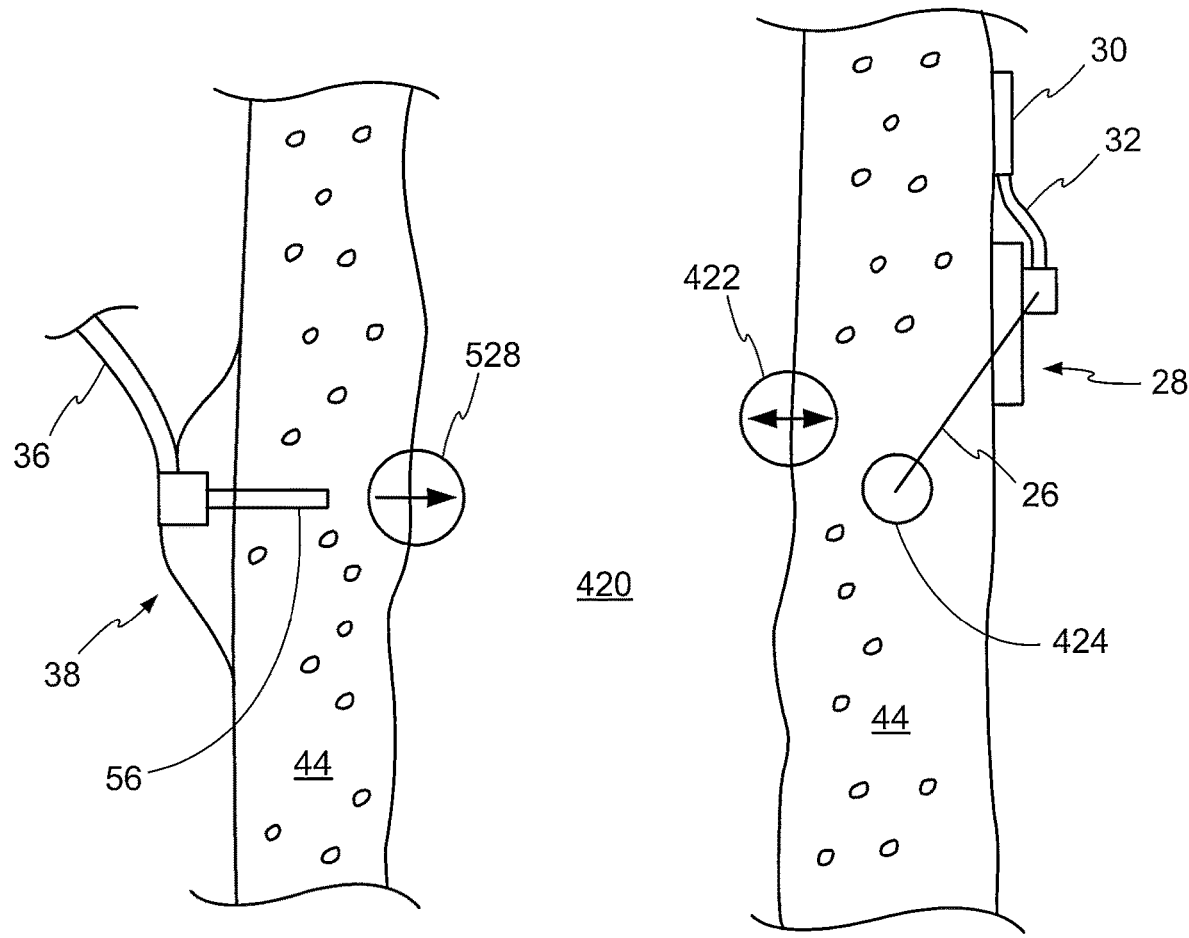
FIG. 7 is a cross-sectional view of an example sensor set and an example infusion set attached to a body in accordance with an embodiment.

FIG. 7 is a cross-sectional view of an example sensor set and an example infusion set that is attached to a body in accordance with an embodiment. In particular example implementations, as shown in FIG. 7, a physiological delay may arise from a time that transpires while glucose moves between blood plasma 420 and interstitial fluid (ISF). This example delay may be represented by a circled double-headed arrow 422. As discussed above with reference to FIG. 2-6, a sensor may be inserted into subcutaneous tissue 44 of body 20 such that electrode(s) 42 (e.g., of FIGS. 3 and 4) near a tip of sensor 40 are in contact with ISF. However, a parameter to be measured may include a concentration of glucose in blood.

Glucose may be carried throughout a body in blood plasma 420. Through a process of diffusion, glucose may move from blood plasma 420 into ISF of subcutaneous tissue 44 and vice versa. As blood glucose level 18 (e.g., of FIG. 1) changes, so does a glucose level of ISF. However, a glucose level of ISF may lag behind blood glucose level 18 due to a time required for a body to achieve glucose concentration equilibrium between blood plasma 420 and ISF. Some studies have shown that glucose lag times between blood plasma and ISF may vary between, e.g., 0 to 30 minutes. Some parameters that may affect such a glucose lag time between blood plasma and ISF are an individual's metabolism, a current blood glucose level, whether a glucose level is rising or falling, combinations thereof, and so forth, just to name a few examples.

A chemical reaction delay 424 may be introduced by sensor response times, as represented by a circle 424 that surrounds a tip of sensor 26 in FIG. 7. Sensor electrodes 42 may be coated with protective membranes that keep electrodes 42 wetted with ISF, attenuate the glucose concentration, and reduce glucose concentration fluctuations on an electrode surface. As glucose levels change, such protective membranes may slow the rate of glucose exchange between ISF and an electrode surface. In addition, there may be chemical reaction delay(s) due to a reaction time for glucose to react with glucose oxidase GOX to generate hydrogen peroxide and a reaction time for a secondary reaction, such as a reduction of hydrogen peroxide to water, oxygen, and free electrons.

Thus, an insulin delivery delay may be caused by a diffusion delay, which may be a time for insulin that has been infused into a tissue to diffuse into the blood stream. Other contributors to insulin delivery delay may include, but are not limited to: a time for a delivery system to deliver insulin to a body after receiving a command to infuse insulin; a time for insulin to spread throughout a circulatory system once it has entered the blood stream; and/or by other mechanical, electrical/electronic, or physiological causes alone or in combination, just to name a few examples. In addition, a body clears insulin even while an insulin dose is being delivered from an insulin delivery system into the body. Because insulin is continuously cleared from blood plasma by a body, an insulin dose that is delivered to blood plasma too slowly or is delayed is at least partially, and possibly significantly, cleared before the entire insulin dose fully reaches blood plasma. Therefore, an insulin concentration profile in blood plasma may never achieve a given peak (nor follow a given profile) that it may have achieved if there were no delay.

Moreover, there may also be a processing delay as an analog sensor signal Isig is converted to digital sensor values Dsig. In particular example embodiments, an analog sensor signal Isig may be integrated over one-minute intervals and converted to a number of counts. Thus, in such a case, an analog-to-digital (A/D) conversion time may result in an average delay of 30 seconds. In particular example embodiments, one-minute values may be averaged into 5-minute values before they are provided to controller 12 (e.g., of FIG. 1). A resulting average delay may be two-and-one-half minutes. In example alternative embodiments, longer or shorter integration times may be used that result in longer or shorter delay times.

In other example embodiments, an analog sensor signal current Isig may be continuously converted to an analog voltage Vsig, and an A/D converter may sample voltage Vsig every 10 seconds. Thus, in such a case, six 10-second values may be pre-filtered and averaged to create a one-minute value. Also, five one-minute values may be filtered and averaged to create a five-minute value that results in an average delay of two-and-one-half minutes. In other alternative embodiments, other sensor signals from other types of sensors may be converted to digital sensor values Dsig as appropriate before transmitting the digital sensor values Dsig to another device. Moreover, other embodiments may use other electrical components, other sampling rates, other conversions, other delay periods, a combination thereof, and so forth.

System Configuration Examples

FIG. 8(a)-8(d) illustrate example diagrams of one or more devices and their components for glucose control systems in accordance with certain embodiments. These FIG. 8(a)-8(d) show exemplary, but not limiting, illustrations of components that may be utilized with certain controller(s) that are described herein above. Various changes in components, layouts of such components, combinations of elements, and so forth may be made without departing from the scope of claimed subject matter.

Before it is provided as an input to controller 12 (e.g., of FIG. 1), a sensor signal 16 may be subjected to signal conditioning such as pre-filtering, filtering, calibrating, and so forth, just to name a few examples. Components such as a pre-filter, one or more filters, a calibrator, controller 12, etc. may be separately partitioned or physically located together (e.g., as shown in FIG. 8(a)), and they may be included with a telemetered characteristic monitor transmitter 30, an infusion device 34, a supplemental device, and so forth.

In particular example embodiments, a pre-filter, filter(s), and a calibrator may be included as part of telemetered characteristic monitor transmitter 30, and a controller (e.g., controller 12) may be included with infusion device 34, as shown in FIG. 8(b). In example alternative embodiments, a pre-filter may be included with telemetered characteristic monitor transmitter 30, and a filter and calibrator may be included with a controller in an infusion device, as shown in FIG. 8(c). In other alternative example embodiments, a pre-filter may be included with telemetered characteristic monitor transmitter 30, while filter(s) and a calibrator are included in supplemental device 41, and a controller may be included in the infusion device, as shown in FIG. 8(d).

In particular example embodiments, a sensor system may generate a message that includes information based on a sensor signal such as digital sensor values, pre-filtered digital sensor values, filtered digital sensor values, calibrated digital sensor values, commands, and so forth, just to name a few examples. Such a message may include other types of information as well, including, by way of example but not limitation, a serial number, an ID code, a check value, values for other sensed parameters, diagnostic signals, other signals, and so forth. In particular example embodiments, digital sensor values Dsig may be filtered in a telemetered characteristic monitor transmitter 30, and filtered digital sensor values may be included in a message sent to infusion device 34 where the filtered digital sensor values may be calibrated and used in a controller. In other example embodiments, digital sensor values Dsig may be filtered and calibrated before transmission to a controller in infusion device 34. Alternatively, digital sensor values Dsig may be filtered, calibrated, and used in a controller to generate commands 22 that are sent from telemetered characteristic monitor transmitter 30 to infusion device 34.

Figure 8:
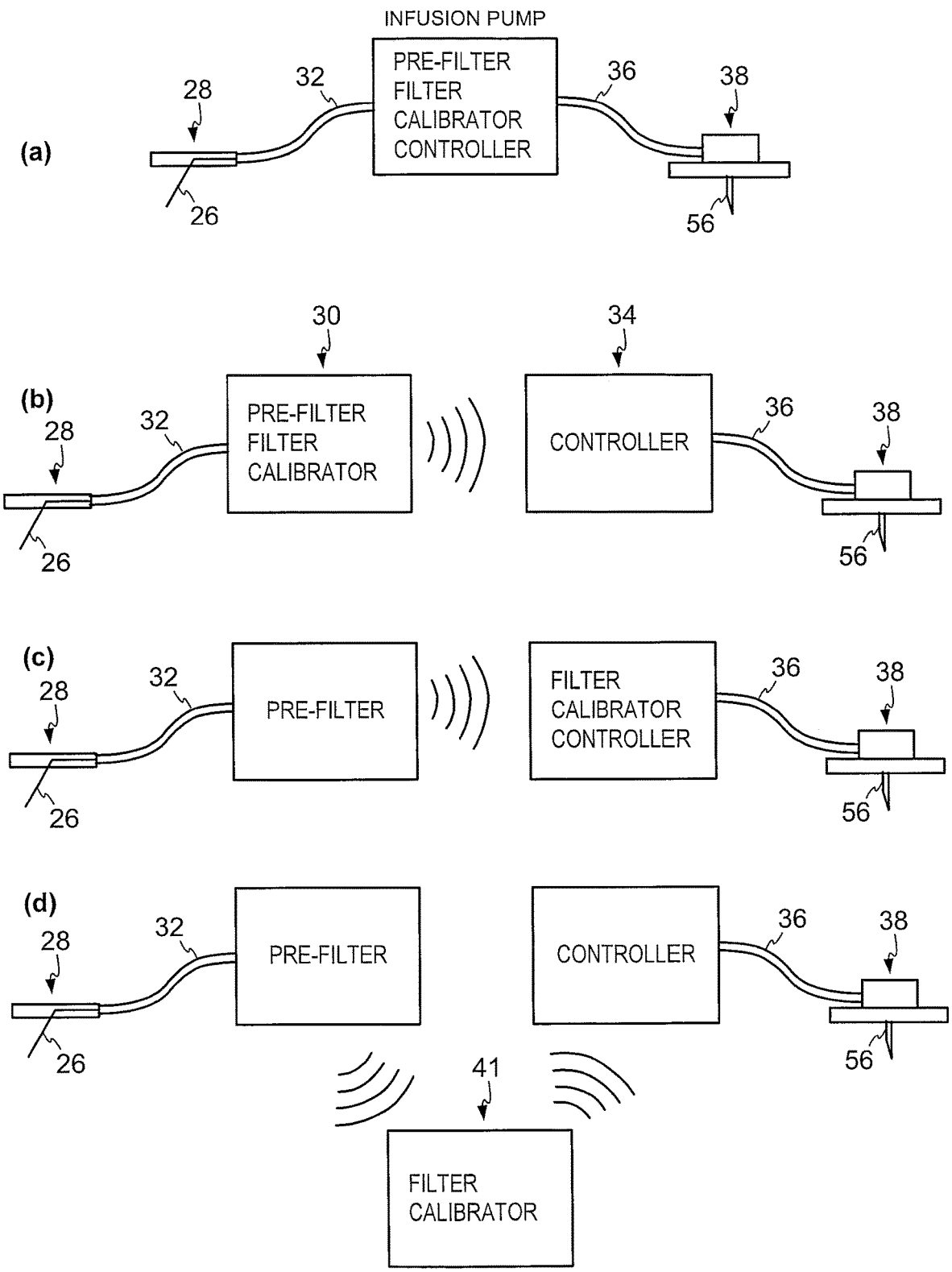
FIG. 8(a) is a diagram of an example single device and its components for a glucose control system in accordance with an embodiment.
FIG. 8(b) is a diagram of two example devices and their components for a glucose control system in accordance with an embodiment.
FIG. 8(c) is another diagram of two example devices and their components for a glucose control system in accordance with an embodiment.
FIG. 8(d) is a diagram of three example devices and their components for a glucose control system in accordance with an embodiment.

In further example embodiments, additional components, such as a post-calibration filter, a display, a recorder, a blood glucose meter, etc. may be included in devices with any of the other components, or they may stand-alone. If a blood glucose meter is built into a device, for instance, it may be co-located in the same device that contains a calibrator. In alternative example embodiments, more, fewer, and/or different components may be implemented than those that are shown in FIG. 8 and/or described herein above.

In particular example embodiments, RF telemetry may be used to communicate between devices that contain one or more components, such as telemetered characteristic monitor transmitter 30 and infusion device 34. In alternative example embodiments, other communication mediums may be employed between devices, such as wires, cables, IR signals, laser signals, fiber optics, ultrasonic signals, and so forth, just to name a few examples.

Example Modes of Operation

Although particular example implementations describe proportional-integral-derivative (PID) control algorithm strategies for use in conjunction with controlling a patient's blood glucose level within a particular range, claimed subject matter is not so limited, as such approaches for controlling a patient's glucose level within a particular range may be implemented with other control strategy or strategies.

As shown in FIG. 9a, according to a particular embodiment, a patient's target glucose range may be defined by three glucose bounds, upper-bound (UB), intermediate-bound (IB), and lower-bound (LB). Here, these three bounds may partition the glucose domain into four zones. Zone 1 represents a region above the UB; zone 2 represents a region between the UB and the IB; the region in between the IB and the LB represents zone 3; finally zone 4 represents the region below the LB. In a particular implementation, a target or set-point glucose level may be established within zone 2 for a patient. In other embodiments, the IB may be set to the predetermined set-point. Here, such a target or set-point blood glucose level may be determined as a target blood glucose $G_B$ as described below. In a particular embodiment, IB, UB and LB may be determined as setoffs from a target or set-point blood glucose level. Here, for example, IB, UB and LB may move along with changes in the set-point or target glucose level.

In an alternative embodiment, a target or set-point blood glucose level may migrate over time into any of the aforementioned zones 1 through 4, while such zones remain fixed. In the particular example shown in FIGS. 9a and 9b, a set-point is located in zone 2. As discussed below in connection with a particular implementation using a PID controller to control an insulin infusion rate, such an insulin infusion rate may be determined based, at least in part, on a predetermined target or set-point blood glucose level.

FIG. 9b shows corresponding actions taken by a controller to infuse insulin to a patient based on and/or responsive to blood glucose levels in the four zones shown in FIG. 9a. Here, it can be observed from FIG. 9b that a constant basal insulin infusion rate is applied while the patient's blood glucose level is in zone 2 as shown in FIG. 9a. While the patient's blood glucose level exceeds UB, an insulin infusion rate is applied according to a controller command (e.g., a PID controller command). While the patient's blood glucose level is in zone 3, insulin infusion is reduced/tapered to below the basal rate until blood glucose drops below LB to be in zone 4. Here, at zone 4, insulin infusion is suspended altogether until blood glucose level exceeds LB to return to zone 3.

According to particular embodiments, $U_{BASAL}$ may be determined by a physician and/or caregiver. Alternatively, $U_{BASAL}$ may be determined by the patient. In one particular implementation, $U_{BASAL}$ may be pre-programmed in an insulin pump to deliver non-meal related insulin. Here, $U_{BASAL}$ may vary throughout the day. Particular values for $U_{BASAL}$ may be determined according to a current standard of care. If glucose levels fall outside of a particular target range, however, an insulin infusion rate may be changed in an attempt to get the blood glucose level back within the target range.

In the particular implementation in which insulin infusion may be controlled by a PID controller, a PID controller command $U_{PUMP}$ may be applied to control an insulin infusion pump on regular command cycles to control an insulin infusion rate. Here, in a particular implementation, treatment to a target blood-glucose range may prevent extreme blood-glucose levels in the absence of action by a patient and/or operator (e.g., to provide a meal bolus) as discussed above.

Processes for determining a PID controller command are expressed herein by way of pseudo code procedures. It should be understood, however, that use of pseudo code is merely one way that such processes may be expressed, and that such processes may be implemented with any one of several techniques without deviating from claimed subject matter. Also, different procedures expressed by pseudo code below need not be executed in any particular order. Further, different procedures expressed by pseudo code below may also executed together or independently of one another. Here, a command $U_{PUMP}$ may be determined on such command cycles according to the following pseudo code procedure:

$$U_{PID} = P + I + D - I_{FB} \quad (1)$$
If (G > UB)
$\quad U_{PUMP} = U_{PID} \quad (2)$
$\quad$ If($U_{PUMP} > U_{max}$)
$\quad\quad U_{PUMP} = U_{max} \quad (3)$
$\quad$ End
$\quad$ If($U_{Tot}^{2h} > TTR_{max}$)
$\quad\quad$ If($U_{PUMP} > U_{BASAL}$)
$\quad\quad\quad U_{PUMP} = U_{BASAL} \quad (4)$
$\quad\quad$ End
$\quad$ End
End In this particular implementation, at expression (1), a PID command $U_{PID}$ may be determined according to a PID algorithm as described below. If it is determined that the patient's blood glucose G exceeds upper bound UB, then the patient's blood glucose is determined to be in zone 1. As such, $U_{PUMP}$ is set to $U_{PID}$ at expression (2).

In the presently illustrated embodiment, $U_{PUMP}$ may be capped at a level $U_{max}$ at expression (3). Here, $U_{max}$ may represent a maximum infusion rate to be allowed according to particular patient safety requirements, for example. In a particular implementation, $U_{max}$ may be set to a level so as to reduce a risk of over infusing insulin. In another embodiment, a command $U_{PUMP}$ to infuse insulin may be bounded based, at least in part, on a total amount of insulin infused to a patient over a particular period. In the presently illustrated embodiment, $U_{Tot}^{2h}$ may represent the total amount of insulin infused to a patient over the past two hours (e.g., determined as a sliding window). Here, as shown in expression (4), $U_{PUMP}$ may be capped at the basal rate $U_{BASAL}$ if $U_{Tot}^{2h}$ exceeds $TTR_{max}$, where $TTR_{max}$ is a predetermined threshold.

According to a particular embodiment, threshold value $TTR_{max}$ may be determined based, at least in part, on a predetermined daily insulin requirement (DIR). In one particular implementation, DIR may be approximated based upon a particular patient's condition as follows:

| Dose (U/kg/day) | Patient's Condition |
| --- | --- |
| 0.5 | trained athlete |
| 0.6 | motivated exerciser |
| 0.7 | adult mildly ill |
| 1.0 | woman at pregnancy |

In another example embodiment, the above values may provide an initial approximation of DIR, and actual values may evolve as based upon glucose control achieved by the patient. In an ambulatory setting, an individual's DIR may be approximated by taking an average/median insulin delivered (per day) over the last several days, for example. It should be understood, however, that these are merely examples of how DIR may be determined, and that claimed subject matter is not limited in this respect.

In one particular implementation, a DailyBolusFraction (e.g., 50%) of DIR may be allocated for daily meal boluses.

This amount may be further divided into three separate meal boluses (e.g., for breakfast, lunch and dinner) and used to determine as follows:

$$TTR_{max} = \frac{DailyBolusFraction \times DIR}{3}.$$

Here, it should be observed that with this particular formulation, decreasing the value of DailyBolusFraction reduces $TTR_{max}$ threshold and may tend to make the algorithm less aggressive. It should be understood, however, that these are merely particular examples of how such a threshold may be determined according to particular embodiments, and that claimed subject matter is not limited in this respect.

As discussed above, while a patient's blood glucose level is in zone 2, a resulting pump infusion rate may be equal to the aforementioned basal rate. However, if blood glucose is decreasing at a rate exceeding a particular threshold, and the PID infusion rate is significantly lower than the basal rate (e.g., $U_{PID} < 0.2 \times U_{BASAL}$, then the pump infusion rate may be switched to the lower PID rate $U_{PID}$. This may be implemented according to the following additional pseudo code procedure:

If (G > IB)& (G < UB)
   $U_{PUMP} = U_{BASAL}$    (5)
   If $\left(\frac{d}{dt}G < -\delta\right)$
     If ($U_{PID} < 0.2 \times U_{BASAL}$)
       $U_{PUMP} = U_{PID}$    (6)
     End
   End
End Here, it can be seen that the above pseudo code procedure enables a PID controller to react early while a patient's blood glucose G is in zone 2 by reducing insulin infusion to below the basal rate if glucose is falling rapidly, thereby potentially reducing the risk of hypoglycemia. In the pseudo code procedure above, a rate of decrease in a patient's blood glucose G is measured by a computation of the derivative $$\frac{d}{dt}G$$

as compared with a threshold value $\delta$. In one particular implementation, $\delta$ may be fixed at a default value, such as 1.0 mg/dl/min. In another particular implementation, $\delta$ may be adjusted based upon clinical data so as to make $\delta$ sufficiently sensitive to allow reaction upon a steep decline in a patient's glucose level, and not overly sensitive in responding to sensor noise. Thus, if while the patient's blood glucose G is in zone 2 and the patient's blood glucose is falling at a rate exceeding $\delta$, expression (6) may set $U_{PUMP}$ to $U_{PID}$ if $U_{PID} < 0.2 \times U_{BASAL}$.

As pointed out above, while a patient's blood glucose G is in zone 3, a pump infusion rate may be determined by the PID command $U_{PID}$. Here, if while a patient's blood glucose G is in zone 3 and blood glucose level is rising, $U_{PUMP}$ may be set to $U_{PID}$ if $U_{PID} < U_{BASAL}$. This may be implemented by the following pseudo code procedure:

If (G > LB)& (G < IB)
   $U_{PUMP} = U_{PID}$    (7)
   If($U_{PUMP} > U_{BASAL}$)
     $U_{PUMP} = U_{BASAL}$    (8)
   End
End

Here, expression (7) sets $U_{PUMP}$ to $U_{PID}$, and expression (8) caps $U_{PUMP}$ at $U_{BASAL}$.

Example Control System Implementations

Figure 10:
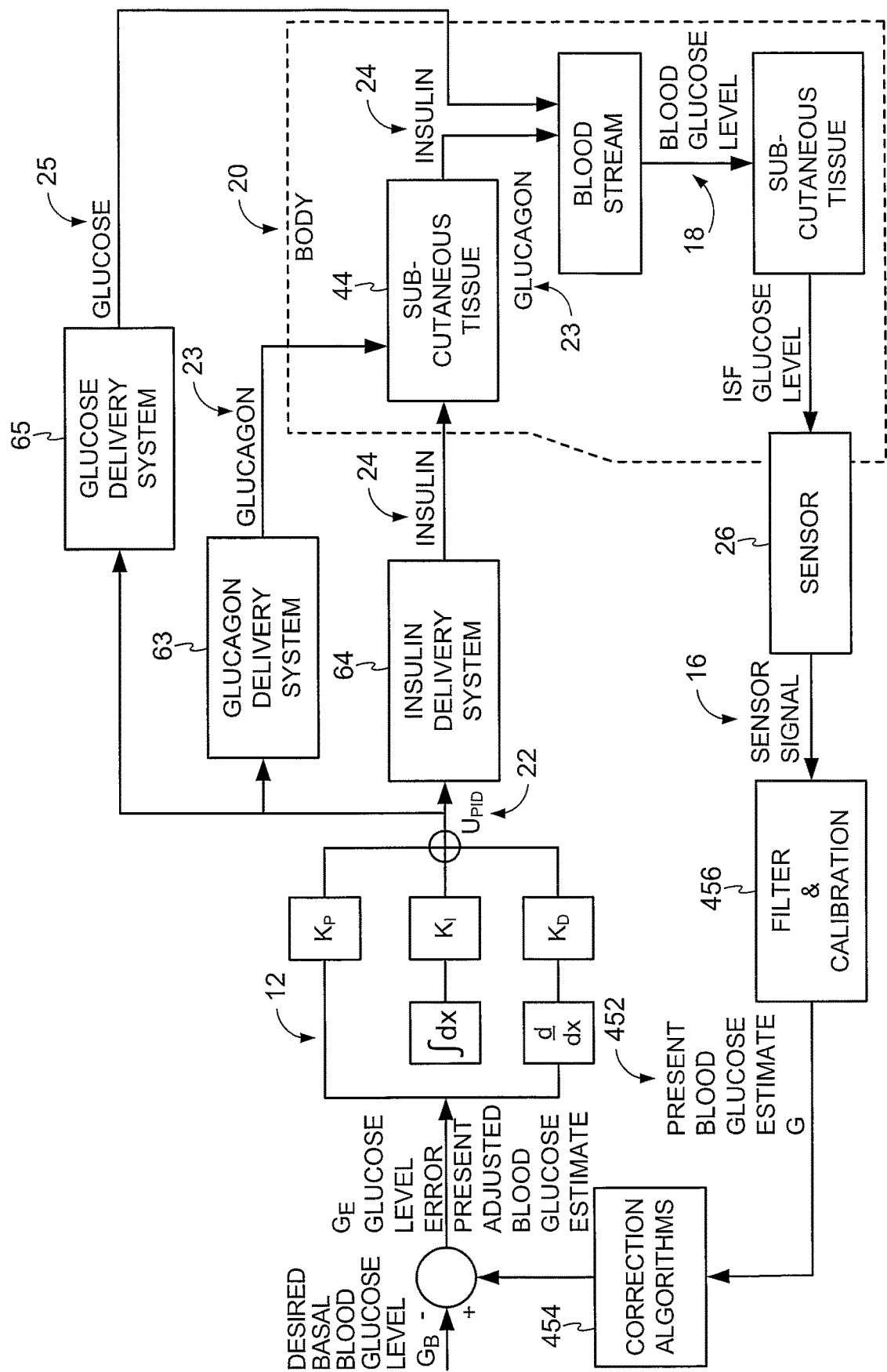
FIG. 10 is a block diagram of an example closed loop system to control blood glucose levels using a proportional-integral-derivative (PID) control algorithm through insulin infusion based on glucose level feedback in accordance with an embodiment.

A controller may be realized for particular example embodiments using any one or more different control algorithm techniques. For instance, controller 12 of FIG. 10 is shown as an example PID controller. Hence, although certain non-exhaustive example embodiments are described herein with regard to a PID controller, other control algorithms may be implemented with a controller.

FIG. 10 is a block diagram of an example closed loop system to control blood glucose levels using a proportional-integral-derivative (PID) control algorithm through at least insulin infusion based on glucose level feedback in accordance with an embodiment. Here, such a closed loop system may be capable of generating a PID command $U_{PID}$ that may be used in part to control the infusion of insulin to a patient. As discussed above, for example, $U_{PID}$ may be used for determining a command $U_{PUMP}$ for controlling a rate of insulin infusion.

In particular example embodiments, a closed loop control system may be used for delivering insulin to a body to compensate for β-cells that perform inadequately. There may be a desired basal or target blood glucose level $G_B$ for a particular body. A difference between a desired basal blood glucose level $G_B$ and an estimate of a present blood glucose level G is the glucose level error $G_E$ that may be corrected. For particular example embodiments, glucose level error $G_E$ may be provided as an input to controller 12, as shown in FIG. 16. Accordingly, a target blood glucose level $G_B$ may be used for used in determining rates of insulin infusion to be applied in controlling a patient's blood glucose level G within specific predefined ranges as discussed above with reference to FIGS. 9a and 9b. In addition to controlling insulin infusion, controller 12 may optionally control rates of delivering glucose and/or glucagon as discussed below.

For certain example embodiments that are described with reference to FIG. 10, controller 12 may be realized as a PID controller. In example implementations, PID controller gains $K_P$, $K_I$, and/or $K_D$ may be selected so that commands from a controller 12 direct insulin delivery system 64 to release insulin 24 into body 20 at a particular rate. Such a particular rate may cause insulin concentration in blood to follow a similar concentration profile as would be caused by fully functioning human p-cells responding to blood glucose concentrations in a body. Optionally, controller gains $K_P$, $K_I$, and/or $K_D$ may be selected so that commands from controller 12 direct glucagon delivery system 63 to release glucagon 23 in response to relatively low glucose levels. Likewise, controller gains $K_P$, $K_I$, and/or $K_D$ may be selected so that commands from controller 12 direct glucose delivery system 65 to release glucose 25 in response to hypoglycemic excursions. In particular example embodiments, controller gains may be selected by observing insulin response(s) of a number of normal glucose tolerant (NGT) individuals having healthy, normally-functioning β-cells. It should be understood, however, that claimed subject matter is not so limited and that controller 12 may be realized in alternative manners, such as with other PID controller implementations, other types of controllers, and so forth, just to name a few examples.

As indicated above in a particular implementation at expression (1), a value for $U_{PID}$ may be determined based, at least in part, on an insulin feedback component $I_{FB}$. Here, incorporation of $I_{FB}$ in the determination of $U_{PID}$ may allow the controller to deliver more insulin in a closed-loop system earlier (e.g., at the onset of a meal), but to prevent over-delivery of insulin. In a closed-loop control system, for example, $I_{FB}$ may act as a lead-lag compensator. In a particular embodiment, $I_{FB}$ may reflect an amount of exogenous insulin in the patient's body infused by the pump. In one example, such an insulin feedback component $I_{FB}$ may be determined based, at least in part, on an insulin absorption model defining three physiological compartments: a subcutaneous compartment; a plasma compartment; and an effective compartment. Here, an insulin feedback component $I_{FB}$ may be determined based, at least in part, on a sum of values associated with these three physiological components as follows:

$$I_{FB} = \gamma_1 \cdot I_{SC} + \gamma_2 \cdot I_P + \gamma_3 \cdot I_{EF},$$

Where:
$I_{SC}$ is insulin in a subcutaneous compartment;
$I_P$ is insulin in a plasma compartment;
$I_{EF}$ is insulin in an effective compartment; and
$\gamma_1, \gamma_2$ and $\gamma_3$ are conversion constants.
Values associated with $I_{SC}$, $I_P$ and $I_{EF}$ may be determined according to the following relations:

$$\frac{d}{dt} I_{SC} = -\frac{1}{\tau_1} I_{SC} + \frac{1}{\tau_1} U_{PUMP}$$

$$\frac{d}{dt} I_P = -\frac{1}{\tau_2} I_P + \frac{1}{\tau_2} I_{SC}$$

$$\frac{d}{dt} I_{EF} = -\frac{1}{\tau_3} I_{EF} + \frac{1}{\tau_3} I_P$$

where $\tau_1, \tau_2$ and $\tau_3$ are time constants

If glucose level error $G_E$ is positive (meaning, e.g., that a present estimate of blood glucose level G is higher than a desired basal blood glucose level $G_B$), then a command from controller 12 may generate a PID command $U_{PID}$ to drive insulin delivery system 64 to provide insulin 24 to body 20. Insulin delivery system 64 may be an example implementation of insulin delivery system 14 (e.g., of FIG. 1). Likewise, if $G_E$ is negative (meaning, e.g., that a present estimate of blood glucose level G is lower than a desired basal blood glucose level $G_B$), then a command from controller 12 may generate a PID command $U_{PID}$ to drive glucagon delivery system 63 to provide glucagon 23 to body 20. Glucagon delivery system 63 may be an example implementation of glucagon delivery system 13 (e.g., of FIG. 1). As pointed out above, a pump command $U_{PUMP}$ may be derived from PID command $U_{PID}$ for controlling insulin delivery to control a patient's blood glucose within target ranges. Optionally, if $G_E$ is negative (meaning, e.g., that a present estimate of blood glucose level G is lower than a desired basal blood glucose level $G_B$), then a command from controller 12 may generate a PID command $U_{PID}$ to drive glucose delivery system 65 to provide glucose 25 to body 20. Glucose delivery system 65 may be an example implementation of glucose delivery system 15 (e.g., of FIG. 1). As shown in FIG. 10, insulin 24 and glucagon 23 are delivered via subcutaneous tissue 44; however, they may alternatively be delivered intravenously. If a patient's blood glucose is below a threshold floor level (which may be below a targeted set point or desired basal blood glucose level $G_B$), then glucose and/or glucagon may be delivered to increase the glucose level of the patient.

Embodiments discussed above are directed to controlling a rate of insulin infusion to maintain a patient's blood glucose level within a target range. In other embodiments, the delivery of glucose and/or glucagon may also be altered to maintain a patient's blood glucose level within a target range.

In terms of a control loop for purposes of discussion, glucose may be considered to be positive, and therefore insulin may be considered to be negative. Sensor 26 may sense an ISF glucose level of body 20 and generate a sensor signal 16. In certain embodiments that are described herein with particular reference to FIG. 10, a control loop may include a filter and calibration unit 456 and/or correction algorithm(s) 454. However, this is by way of example only, and claimed subject matter is not so limited. Sensor signal 16 may be filtered and calibrated at unit 456 to create an estimate of present blood glucose level 452. In particular example embodiments, an estimate of present blood glucose level G may be adjusted with correction algorithms 454 before it is compared to a desired basal blood glucose level $G_B$ to calculate a new glucose level error $G_E$ to start a loop again. Also, an attendant, a caretaker, a patient, etc. may obtain blood glucose reference measurements from a patient's blood using, e.g., glucose test strips. These blood-based measurements may be used to calibrate ISF-based sensor measurements using techniques, e.g., such as those described in U.S. Pat. No. 6,895,263, issued 17 May 2005.

If a glucose level error $G_E$ is negative (meaning, e.g., that a present estimate of blood glucose level is lower than a desired basal blood glucose level $G_B$), then controller 12 may reduce or stop insulin delivery depending on whether an integral component response of a glucose error $G_E$ is still positive. In alternative embodiments, as discussed below, controller 12 may initiate infusion of glucagon 23 and/or glucose 25 if glucose level error $G_E$ is negative. If a glucose level error $G_E$ is zero (meaning, e.g., that a present estimate of blood glucose level is equal to a desired basal blood glucose level $G_B$), then controller 12 may or may not issue commands to infuse insulin 24, glucagon 23, and/or glucose 25, depending on a derivative component (e.g., whether glucose level is raising or falling) and/or an integral component (e.g., how long and by how much glucose level has been above or below basal blood glucose level $G_B$).

To more clearly understand the effects that a body has on such a control loop, a more detailed description of physiological effects that insulin has on glucose concentration in ISF is provided. In particular example embodiments, insulin delivery system 64 may deliver insulin 24 into ISF of subcutaneous tissue 44 (e.g., also of FIGS. 3, 4, and 6) of body 20. Alternatively, insulin delivery system 64 or one or more separate infusion device(s) (e.g., glucagon delivery system 63 and/or glucose delivery system 65) may similarly deliver glucagon 23 into ISF of subcutaneous tissue 44 and/or deliver glucose 25 into an intravenous cavity of a blood stream. Here, insulin and/or glucagon may diffuse from local ISF surrounding a cannula into blood plasma and spread throughout body 20 in a main circulatory system. Infused insulin and/or glucagon may diffuse from blood plasma into ISF substantially throughout the entire body.

Here in the body, insulin 24 may bind with and activate membrane receptor proteins on cells of body tissues. This may facilitate glucose permeation into activated cells. In this way, tissues of body 20 may take up glucose from ISF. As ISF glucose level decreases, glucose may diffuse from blood plasma into ISF to maintain glucose concentration equilibrium. Glucose in ISF may permeate a sensor membrane of sensor 26 and affect sensor signal 16.

In addition, insulin may have direct and indirect effects on liver glucose production. Typically, increased insulin concentration may decrease liver glucose production. Therefore, acute and immediate insulin response may not only help a body to efficiently take up glucose, but it may also substantially stop a liver from adding to glucose in the blood stream. In alternative example embodiments, as pointed out above, insulin, glucagon, and/or glucose may be delivered more directly into the blood stream instead of into ISF, such as by delivery into veins, arteries, the peritoneal cavity, and so forth, just to name a few examples. Accordingly, any time delay associated with moving insulin, glucagon, and/or glucose from ISF into blood plasma may be diminished. In other alternative example embodiments, a glucose sensor may be in contact with blood or other body fluids instead of ISF, or a glucose sensor may be outside of a body such that it may measure glucose through non-invasive means. Embodiments using alternative glucose sensors may have shorter or longer delays between an actual blood glucose level and a measured blood glucose level.

Example PID Controller Implementations for Example Embodiments

A general equation that is usable for a PID algorithm is given by expression (9):

$$u(t) = \underbrace{K_P e(t)}_{Proportional} + \underbrace{\frac{K_P}{\tau_I} \int_0^t e(\tau)\, d\tau}_{Integral} + \underbrace{K_P \tau_D \frac{de(t)}{dt}}_{Derivative} \quad (9)$$

where u(t) may be a manipulated variable used to regulate a system and $e(t) = G_S(t) - G_B(t)$ may be an error signal. An error signal may be a difference between a set point ($G_B(t)$, a target where a controlled variable is desired to be at) and a controlled variable ($G_S(t)$). PID tuning parameters may include a controller gain ($K_P$), an integral time constant ($\tau_I$), and a derivative time constant ($\tau_D$). A proportional term adjusts a manipulated variable in proportion to an error at a given time. An integral term adjusts a manipulated variable in proportion to an accumulated error (e.g., modeled by an integral) as averaged over a time period specified by $\tau_I$. Thus, as $\tau_I$ is increased, this integral component may have a lesser or lower effect on overall control action. A derivative term adjusts a manipulated variable in proportion to a derivative of an error. Multiplication by $\tau_D$ can be viewed as a projection of an error into the future if a current rate of change persists; therefore, having a larger $\tau_D$ may result in a stronger or higher change to the control action.

If insulin feedback is also incorporated into a PID algorithm, an insulin pharmacokinetic model may be initialized by utilizing prior insulin delivery. Such insulin-on-board may also be used to impose additional constraints on controller action, thereby incorporating open-loop history. According to an embodiment, insulin-on-board may be modeled as having three distinct components or compartments: a subcutaneous compartment $IOB_S(t)$; a plasma compartment $IOB_P(t)$; and an effect site compartment $IOB_E(t)$. One or more of these components may be independently estimated according to an insulin pharmacokinetic model.

An insulin pharmacokinetic model may be incorporated into determination of a PID command $U_{PID}$ by reducing an amount of insulin to be infused based, at least in part, on estimates of insulin-on-board. One of the particular challenges to delivering insulin to control a patient's blood glucose G to within a range is not to over-deliver insulin following a nominal pre-meal bolus while the patient's blood glucose is in zone 1 and still rising (FIGS. 9a and 9b). Extra insulin from the meal bolus may be reflected in insulin feedback. However, insulin feedback may not be adequate to suppress $U_{PID}$ to prevent over-delivery of insulin. Here, in a particular implementation, application of the following pseudo code procedure may account for excess insulin on board and tend to make the PID procedure less aggressive: One particular approach considers insulin-on-board in a plasma compartment according to the following pseudo code procedure:

If ($IOB_{BOLUS}$ > Minimum $IOB_{BOLUS}$)
    ExtraIOB$_{BOLUS}$ = $\tau_{IOB}$ × $IOB_{BOLUS}$ − $U_{BASAL}$    (10)
Else
    ExtraIOB$_{BOLUS}$ = 0    (11)
End
If (ExtraIOB$_{BOLUS}$ < 0 )
    ExtraIOB$_{BOLUS}$ = 0    (12)
End
$U_{PID}$ = $U_{PID}$ − ExtraIOB$_{BOLUS}$    (13)

where:

$IOB_{BOLUS}$ is insulin-on-board in the plasma compartment due to manual bolus;

$\tau_{IOB}$ is a rate constant which converts $IOB_{BOLUS}$ to a rate (e.g., from U to U/h);

Minimum $IOB_{BOLUS}$ is a minimum insulin-on-board in the plasma compartment in due to manual bolus (e.g., 1.0 U of insulin); and ExtraIOB$_{BOLUS}$ is insulin-on-board in excess of a basal rate.

Here, ExtraIOB$_{BOLUS}$ is calculated based upon a rate constant $\tau_{IOB}$ applied to insulin-on-board in the plasma compartment due to manual bolus, where the rate constant reflects a rate at which ExtraIOBp$_{BOLUS}$ is absorbed by the patient.

While the particular approach considers a specific manner of calculating/estimating insulin-on-board in a plasma compartment, it should be understood that insulin-on-board may be calculated/estimated using any one of several different techniques without deviating from claimed subject matter.

Example Embodiments for Specifying a Target Blood Glucose Reference Trajectory

For certain example embodiments, a blood glucose reference trajectory may be based on reasonable performance expectations that are founded on known physiology, pharmacokinetics, and pharmacodynamics of insulin. The greater a measured blood glucose concentration is above a targeted blood glucose level, the more likely establishing a blood glucose reference trajectory is to be helpful in avoiding a hypoglycemic event. Many different approaches may be employed to define a blood glucose reference trajectory that is initially rising or falling. Example approaches for defining a reference trajectory to target for blood glucose levels include, but are not limited to: a simple exponential decay curve, a second order response, a model-based expected response from a correction bolus considering starting conditions, a combination thereof, and so forth. After glucose levels stop rising after entering zone 1, a reference trajectory may be established to cause the algorithm to attempt to cause a measured blood glucose concentration of patient to track the reference trajectory. Thus, for particular example implementations, a second order response may be used that starts at a glucose level when glucose stops rising after entering zone 1. A target or set-point blood glucose reference trajectory in this case may be described mathematically as shown by expression (14):

$$G_B(t) = \frac{G_S(t_0) - G_B}{\tau_1 - \tau_2}\left(\tau_1 e^{\frac{-t}{\tau_1}} - \tau_2 e^{\frac{-t}{\tau_2}}\right) + G_B \quad (14)$$

where $G_B(t)$ may be a glucose set-point and/or target as a function of time, $G_S(t_0)$ may be a sensor glucose value at the time when glucose levels stop rising $(t_0)$, $G_B$ may be a fixed set-point and/or target after an initial period, and $\tau_1$ and $\tau_2$ may be time constants that define a desired response. Such time constants may be set so that a reference trajectory is adequate from a clinical perspective. It should be understood that the particular process for determining a target blood glucose level and/or blood glucose set-point described above is merely an example process, and that other such processes may be used for determining a target blood glucose level and/or blood glucose set-point without deviating from claimed subject matter.

Because this particular reference trajectory is specified analytically in this way, its rate of change can also be derived analytically. This rate of change may be used explicitly in, e.g., a derivative term of a PID algorithm. However, reference trajectories may be implemented in alternative manners.

In a particular implementation, zones 1 through zone 4 as shown in FIGS. 9*a* and 9*b* may be defined relative to a variable set-point and/or target glucose level. In one particular example, boundaries IB, UP and LB between such zones may move over time in response to particular changes in a target or set-point glucose level.

Unless specifically stated otherwise, as is apparent from the preceding discussion, it is to be appreciated that throughout this specification discussions utilizing terms such as "processing", "computing", "calculating", "determining", "estimating", "selecting", "identifying", "obtaining", "representing", "receiving", "transmitting", "storing", "analyzing", "associating", "measuring", "detecting", "controlling", "delaying", "initiating", "setting", "delivering", "waiting", "starting", "providing", and so forth may refer to actions, processes, etc. that may be partially or fully performed by a specific apparatus, such as a special purpose computer, special purpose computing apparatus, a similar special purpose electronic computing device, and so forth, just to name a few examples. In the context of this specification, therefore, a special purpose computer or a similar special purpose electronic computing device may be capable of manipulating or transforming signals, which are typically represented as physical electronic and/or magnetic quantities within memories, registers, or other information storage devices; transmission devices; display devices of a special purpose computer; or similar special purpose electronic computing device; and so forth, just to name a few examples. In particular example embodiments, such a special purpose computer or similar may comprise one or more processors programmed with instructions to perform one or more specific functions. Accordingly, a special purpose computer may refer to a system or a device that includes an ability to process or store data in the form of signals. Further, unless specifically stated otherwise, a process or method as described herein, with reference to flow diagrams or otherwise, may also be executed or controlled, in whole or in part, by a special purpose computer.

It should be noted that although aspects of the above systems, methods, devices, processes, etc. have been described in particular orders and in particular arrangements, such specific orders and arrangements are merely examples and claimed subject matter is not limited to the orders and arrangements as described. It should also be noted that systems, devices, methods, processes, etc. described herein may be capable of being performed by one or more computing platforms. In addition, instructions that are adapted to realize methods, processes, etc. that are described herein may be capable of being stored on a storage medium as one or more machine readable instructions. If executed, machine readable instructions may enable a computing platform to perform one or more actions. "Storage medium" as referred to herein may relate to media capable of storing information or instructions which may be operated on, or executed by, one or more machines (e.g., that include at least one processor). For example, a storage medium may comprise one or more storage articles and/or devices for storing machine-readable instructions or information. Such storage articles and/or devices may comprise any one of several media types including, for example, magnetic, optical, semiconductor, a combination thereof, etc. storage media. By way of further example, one or more computing platforms may be adapted to perform one or more processes, methods, etc. in accordance with claimed subject matter, such as methods, processes, etc. that are described herein. However, these are merely examples relating to a storage medium and a computing platform and claimed subject matter is not limited in these respects.

Although what are presently considered to be example features have been illustrated and described, it will be understood by those skilled in the art that various other modifications may be made, and equivalents may be substituted, without departing from claimed subject matter. Additionally, many modifications may be made to adapt a particular situation to the teachings of claimed subject matter without departing from central concepts that are described herein. Therefore, it is intended that claimed subject matter not be limited to particular examples disclosed, but that such claimed subject matter may also include all aspects falling within the scope of appended claims, and equivalents thereof.

What is claimed is:

1. A method comprising:
    establishing a blood glucose set-point for a patient;
    establishing a range about the blood glucose set-point, the range being defined, at least in part, by a first bound greater than the blood glucose set-point and a second bound less than the blood glucose set-point;
    delivering insulin to the patient using an infusion device at a first insulin delivery rate while a first estimated blood glucose level of the patient at a first point in time is within the range;
    determining by one or more processors that a second estimated blood glucose level of the patient at a second point in time is greater than the first bound or less than the second bound;
    applying by the one or more processors a second insulin delivery rate at which to deliver insulin to the patient using the infusion device in response to the determination by the one or more processors that the second estimated blood glucose level of the patient at the second point in time is greater than the first bound or less than the second bound, the second insulin delivery rate being different from the first insulin delivery rate and the second insulin delivery rate being applied by the one or more processors based, at least in part, on the blood glucose set-point;

determining by the one or more processors that a third estimated blood glucose level of the patient at a third point in time is decreasing at a rate exceeding a threshold and that the third estimated blood glucose level is less than the first bound and greater than a third bound that is between the blood glucose set-point and the second bound; and applying by the one or more processors a third insulin delivery rate at which to deliver insulin to the patient using the infusion device in response to the determination by the one or more processors that the third estimated blood glucose level of the patient at the third point in time is decreasing at the rate exceeding the threshold and that the third estimated blood glucose level is less than the first bound and greater than the third bound, the third insulin delivery rate being different from the first and second insulin delivery rates, and the third insulin delivery rate being applied by the one or more processors based, at least in part, on the blood glucose set-point, wherein the first, second and third estimated blood glucose levels of the patient are based, at least in part, upon signals of a blood glucose sensor in contact with the patient.

2. The method of claim 1, wherein the range is determined based, at least in part, on a predetermined daily insulin requirement established for the patient.

3. The method of claim 1, and further comprising applying the second insulin delivery rate in response to a prediction that a fourth estimated blood glucose level of the patient at a fourth point in time is to be outside of the range.

4. The method of claim 1, wherein the second insulin delivery rate is less than the first insulin delivery rate if the second estimated blood glucose level is below the range.

5. The method of claim 4, wherein the second insulin delivery rate comprises a zero insulin infusion rate.

6. The method of claim 1, wherein the second and third insulin delivery rates are based, at least in part, on a PID algorithm.

7. The method of claim 1, and further comprising:
applying the first insulin delivery rate while a fourth estimated blood glucose level of the patient at a fourth point in time is above the range if insulin delivered to the patient over a sliding window exceeds a threshold amount.

8. The method of claim 1, wherein the blood glucose set-point is determined based, at least in part, on a reference trajectory.

9. The method of claim 1, and further comprising receiving commands from the patient to determine the first insulin delivery rate, and wherein the applying the second insulin delivery rate to the patient further comprises applying the second insulin delivery rate in an absence of at least one command received from the patient after receiving the commands to determine the first insulin delivery rate.

10. The method of claim 1, and further comprising delivering glucose to the patient while a fourth estimated blood glucose level of the patient at a fourth point in time is less than the second bound.

11. The method of claim 1, and further comprising delivering glucagon to the patient while a fourth estimated blood glucose level of the patient at a fourth point in time is less than the second bound.

12. An article for use with an infusion device containing insulin and attached to a patient, and for use with a blood glucose sensor in contact with the patient and configured to generate signals, the article comprising:

a storage medium comprising machine-readable instructions stored thereon which are executable by a special purpose computing apparatus to:

initiate application by the infusion device of the insulin to the patient at a first insulin delivery rate while a first estimated blood glucose level of the patient at a first point in time is within a range about a blood glucose set-point for the patient, wherein the range is defined, at least in part, by a first bound greater than the blood glucose set-point and a second bound less than the blood glucose set-point;

determine that a second estimated blood glucose level of the patient at a second point in time is greater than the first bound or less than the second bound;

initiate application of a second insulin delivery rate at which to deliver insulin to the patient using the infusion device in response to the determination by the special purpose computing apparatus that the second estimated blood glucose level of the patient at the second point in time is greater than the first bound or less than the second bound, the second insulin delivery rate being different from the first insulin delivery rate and applied by the special purpose computing apparatus based, at least in part, on the blood glucose set-point;

determine that a third estimated blood glucose level of the patient at a third point in time is decreasing at a rate exceeding a threshold and that the third estimated blood glucose level is less than the first bound and greater than a third bound that is between the blood glucose set-point and the second bound; and initiate application of a third insulin delivery rate at which to deliver insulin to the patient using the infusion device in response to the determination by the special purpose computing apparatus that the third estimated blood glucose level of the patient at the third point in time is decreasing at the rate exceeding the threshold and that the third estimated blood glucose level is less than the first bound and greater that the third bound, wherein the third insulin delivery rate is different from the first and second insulin delivery rates and is applied by the special purpose computing apparatus based, at least in part, on the blood glucose set-point, and wherein the first, second and third estimated blood glucose levels of the patient are based, at least in part, upon the signals of the blood glucose sensor in contact with the patient.

13. The article of claim 12, wherein the second and third insulin delivery rates are based, at least in part, on a PID algorithm.

14. The article of claim 12, wherein the instructions are further executable by the special purpose computing apparatus to initiate application by the infusion device of the second insulin delivery rate in response to a prediction that a fourth estimated blood glucose level of the patient at a fourth point in time is to be outside of the range.

15. The article of claim 12, wherein the instructions are further executable by the special purpose computing apparatus to initiate application by the infusion device of the first insulin delivery rate while a fourth estimated blood glucose level of the patient at a fourth point in time is above the range if insulin delivered to the patient over a sliding window exceeds a threshold amount.

16. An apparatus for use with an infusion device containing insulin and attached to a patient, the apparatus comprising:
- a blood-glucose sensor configured to generate a sensor signal representative of a blood glucose level in the patient; and
- a controller adapted to:
- initiate application by the infusion device of the insulin to the patient at a first insulin delivery rate while an estimate of a first blood glucose level of the patient at a first point in time is within a range about a blood glucose set-point for the patient, the estimate of the first blood glucose level being based, at least in part, on the sensor signal, and wherein the range is defined, at least in part, by a first bound greater than the blood glucose set-point and a second bound less than the blood glucose set-point;
- determine that a second estimated blood glucose level of the patient at a second point in time is greater than the first bound or less than the second bound;
- initiate application of a second insulin delivery rate at which to deliver insulin to the patient using the infusion device in response to the determination by the controller that the second estimated blood glucose level of the patient at the second point in time is greater than the first bound or less than the second bound, the second insulin delivery rate being applied by the controller based, at least in part, on the blood glucose set-point, wherein the second insulin delivery rate is different from the first insulin delivery rate;
- determine that a third estimated blood glucose level of the patient at a third point in time is decreasing at a rate exceeding a threshold and that the third estimated blood glucose level is less than the first bound and greater than a third bound that is between the blood glucose set-point and the second bound; and
- initiate application of a third insulin delivery rate at which to deliver insulin to the patient using the infusion device in response to the determination by the controller that the third estimated blood glucose level of the patient at the third point in time is decreasing at the rate exceeding the threshold and that the third estimated blood glucose level is less than the first bound and greater that the third bound, wherein the third insulin delivery rate is different from the first and second insulin delivery rates and is applied by the controller based, at least in part, on the blood glucose set-point.

17. The apparatus of claim 16, wherein the controller is further adapted to receive commands from the patient to determine insulin delivery, and initiate application of the second insulin delivery rate to the patient in an absence of receipt of a command at the controller.

* * * * *